United States Patent
Gudkov

(10) Patent No.: US 10,406,206 B2
(45) Date of Patent: *Sep. 10, 2019

(54) PROTECTION AGAINST STRESS-MEDIATED DAMAGE FROM IONIZING RADIATION

(71) Applicant: The Cleveland Clinic Foundation, Cleveland, OH (US)

(72) Inventor: Andrei V. Gudkov, Buffalo, NY (US)

(73) Assignee: The Cleveland Clinic Foundation, Cleveland, OH (US)

(*) Notice: Subject to any disclaimer, the term of this patent is extended or adjusted under 35 U.S.C. 154(b) by 167 days.

This patent is subject to a terminal disclaimer.

(21) Appl. No.: 15/413,949

(22) Filed: Jan. 24, 2017

(65) Prior Publication Data
US 2017/0128533 A1    May 11, 2017

Related U.S. Application Data

(60) Continuation of application No. 15/049,953, filed on Feb. 22, 2016, now Pat. No. 9,585,939, which is a continuation of application No. 14/305,709, filed on Jun. 16, 2014, now Pat. No. 9,296,793, which is a continuation of application No. 12/617,653, filed on Nov. 12, 2009, now Pat. No. 8,784,840, which is a division of application No. 11/421,918, filed on Jun. 2, 2006, now Pat. No. 7,638,485, which is a continuation of application No. PCT/US2004/040579, filed on Dec. 2, 2004, which is a continuation of application No. PCT/US2004/040753, filed on Dec. 2, 2004, which is a continuation of application No. PCT/US2004/040749, filed on Dec. 2, 2004, which is a continuation of application No. PCT/US2004/040750, filed on Dec. 2, 2004.

(60) Provisional application No. 60/526,666, filed on Dec. 2, 2003, provisional application No. 60/526,496, filed on Dec. 2, 2003, provisional application No. 60/526,460, filed on Dec. 2, 2003, provisional application No. 60/526,461, filed on Dec. 2, 2003.

(51) Int. Cl.

| | | |
|---|---|---|
| A61K 38/18 | (2006.01) | |
| A61K 38/16 | (2006.01) | |
| A61K 38/19 | (2006.01) | |
| G01N 33/50 | (2006.01) | |
| A61K 31/355 | (2006.01) | |
| A61K 31/568 | (2006.01) | |
| A61K 31/661 | (2006.01) | |
| C07K 14/255 | (2006.01) | |
| A61K 45/06 | (2006.01) | |

(52) U.S. Cl.
CPC ........ *A61K 38/1841* (2013.01); *A61K 31/355* (2013.01); *A61K 31/568* (2013.01); *A61K 31/661* (2013.01); *A61K 38/164* (2013.01); *A61K 38/18* (2013.01); *A61K 38/19* (2013.01); *A61K 45/06* (2013.01); *C07K 14/255* (2013.01); *G01N 33/502* (2013.01); *G01N 2333/4703* (2013.01); *G01N 2333/4748* (2013.01); *G01N 2333/495* (2013.01); *G01N 2500/00* (2013.01); *Y02A 50/481* (2018.01)

(58) Field of Classification Search
None
See application file for complete search history.

(56) References Cited

U.S. PATENT DOCUMENTS

| | | |
|---|---|---|
| 5,399,494 A | 3/1995 | Kaper et al. |
| 6,130,082 A | 10/2000 | Majarian et al. |
| 7,638,485 B2 | 12/2009 | Gudkov |
| 8,106,005 B2 | 1/2012 | Gudkov |
| 8,287,882 B2 | 10/2012 | Gudkov et al. |
| 8,784,840 B2 | 7/2014 | Gudkov |
| 2006/0275255 A1 | 12/2006 | Gudkov |
| 2010/0056454 A1 | 3/2010 | Gudkov |

OTHER PUBLICATIONS

Alavanja, Michael C.R., "Biologic Damage Resulting from Exposure to Tobacco Smoke and from Radon: Implication for Preventive Interventions", Oncogene, vol. 21, No. 48, Oct. 21, 2002, pp. 7365-7375.
Andreassen et al., "Chemical Radioprotection: a Critical Review of Amifostine as a Cytoprotector in Radiotherapy", Seminars in Radiation Oncology, vol. 13, No. 1, Jan. 2003, pp. 62-72.
"Androstenediol and Androstenedione", Wikipedia. http://enwikipedia.org/wiki. Retrieved from the Internet: Dec. 5, 2006, 4 pages
Bachmann, et al., "Recall Proliferation Potential of Memory CD8+ T Cells and Antiviral Protection", The Journal of Immunology, vol. 175, Oct. 2005, pp. 4677-4585.
Borges et al., "DNA Damage-Induced Cell Death: Lessons from the Central Nervous System", Cell Research, vol. 18, No. 1, Jan. 2008, pp. 17-26.
Burdelya et al., "An Agonist of Toll-Like Receptor 5 Has Radioprotective Activity in Mouse and Primate Models", Science, vol. 320, No. 5873, Apr. 11, 2008, pp. 226-230.
Barnes, Bruce A. et al. "Mortality of Atomic Bomb Survivors Predicted from Laboratory Animals", Radiation Research, vol. 160, No. 2, Aug. 2003, pp. 159-167 (Abstract only).

(Continued)

*Primary Examiner* — Alana Harris Dent
(74) *Attorney, Agent, or Firm* — Morgan, Lewis & Bockius LLP

(57) ABSTRACT

The use and screening of modulators of apoptosis is disclosed. The modulators may be, for example, modulator of NF-κB activity. The modulators may be used, for example, in the treatment of NF-κB-mediated diseases, conditions, and injuries.

4 Claims, 19 Drawing Sheets

(56) References Cited

OTHER PUBLICATIONS

Cholera, "Cholera", Wikipedia, 2008.
Das, Undurti N., "A Radical Approach to Cancer", Medical Science Monitor, vol. 8, No. 4, Apr. 2002, pp. RA79-RA92.
Definition of Prophylaxis, "Merriam-Webster Medical Dictionary", online edition, 2005.
Definition of Prophylaxis, "Stedman's Medical Dictionary", 27th edition online, 2000.
Eaves-Pyles et al., "*Salmonella Flagellin*-Dependent Proinflammatory Responses Are Localized to the Conserved Amino and Carboxyl Regions of the Protein", The Journal of Immunology, vol. 167, No. 12, 2001, pp. 7009-7016.
Efferson, et al., "Stimulation of Human T Cells by an Influenza A Vector Expressing a CTL Epitope from the HER-2/neu Protooncogene results in higher Nembers of Antigen-Specific TCRhi Cells than Stimulation with Eptide. Divergent Roles of IL-2 and IL-15", Anticancer Res. vol. 25, No. 2A, Mar.-Apr. 2005, pp. 715-724.
Haimovitz-Friedman et al., "Ionizing Radiation Acts on Cellular Membranes to Generate Ceramide and Initiate Apoptosis", The Journal of Experimental Medicine, vol. 180, No. 2, Aug. 1, 1994, pp. 525-535.
Hall et al., "Physics and Chemistry of Radiation Absorption", Radiobiology for the Radiobiologist, 5th Edition, Philadelphia: Lippincott Williams Wilkins, 2000, pp. 5-15.
Lehnert et al., "A New Mechanism for DNA Alterations Induced by Alpha Particles Such as Those Emitted by Radon and Radon Progeny", Environmental Health Perspectives, vol. 105, No. 5, Sep. 1997, pp. 1095-1101.
Li et al. "A Special Issue on DNA Damage Responses and Genome Maintenance", Cell Research, vol. 18, Jan. 7, 2008, pp. 1-2.
Mutlu-Türkoĝlu et al., "The Effect of Selenium and/or Vitamin E Treatments on Radiation-Induced Intestinal Injury in Rats", Life Sciences, vol. 66, No. 20, Apr. 7, 2000, pp. 1905-1913.
Patchen, M. L., "Amifostine plus Granulocyte Colony-Stimulating Factor Therapy Enhances Recovery from Supralethal Radiation Exposures: Preclinical Experience in Animals Models", European Journal of Cancer, vol. 31, No. 1, 1995, pp. S17-S21.
Satyamitra et al., "In Vivo Postirradiation Protection by a Vitamin E Analog, Alpha-TMG", Radiat Res. vol. 160, No. 6, Dec. 2003, pp. 655-661.
Seed et al., "New Strategies for the Prevention of Radiation Injury: Possible Implications for Countering Radiation. Hazards of Long-term Space Travel", Journal of Radiation Research, vol. 43, 2002, pp. S239-S244.
Sredini et al., "The Immunomodulator AS101 Administered Orally as a Chemoprotective and Radioprotective Agent", International Journal of Immunopharmacology, vol. 14, No. 4, May 1992, pp. 613-619.
Streeter et al., "Activation of the G-CSF and Flt-3 Receptors Protects Hematopoietic Stem Cells from Lethal Irradiation", Experimental Hematology, vol. 31, No. 11, Nov. 2003, pp. 1119-1125.
Symon et al., "Selective Radioprotection of Hepatocytes by Systemic and Portal Vein Infusions of Amifostine in a Rat Liver Tumor Model", International Journal of Radiation Oncology, Biology, Physics, vol. 50, No. 2, Jun. 1, 2001, pp. 473-478.
Waddick et al., "In Vitro and In Vivo Antileukemic Activity of B43-Pokeweed Antiviral Protein against Radiation-Resistant Human B-Cell Precursor Leukemia Cells", Blood, vol. 86, No. 11, Dec. 1, 1995, pp. 4228-4233.
Wheeler, Cosette M., "Preventive Vaccines for Cervical Cancer", Salud Publica de Mexico, vol. 39, No. 4, Jul.-Aug. 1997, pp. 1-5.
Whitnall et al., "In Vivo Radioprotection by 5-Androstenediol: Stimulation of the Innate Immune System", Radiation Research, vol. 156, No. 3, Sep. 2001, pp. 283-293.
Wikipedia, "Sunburn", available at http://en.wikipedia.org/w/index.php?oldid=456282380, Nov. 15, 2011.
Wikipedia, "Ultraviolet", available at http://en.wikipedia.org/w/index.php?oldid=460695105, Nov. 15, 2011.
Wong, Grace H.W., "Protective Roles of Cytokines against Radiation: Induction of Mitochondrial MnSOD", Biochimlca et Biophysica Acta, vol. 1271, No. 1, 1995, pp. 205-209.
Mercurio F., "NF-kB as a primary regulator of the stress response," Oncogene, 1999, 18:6163-71.

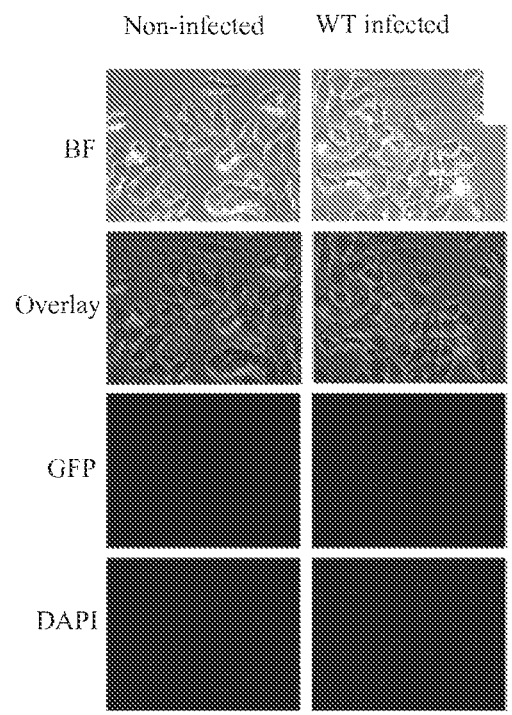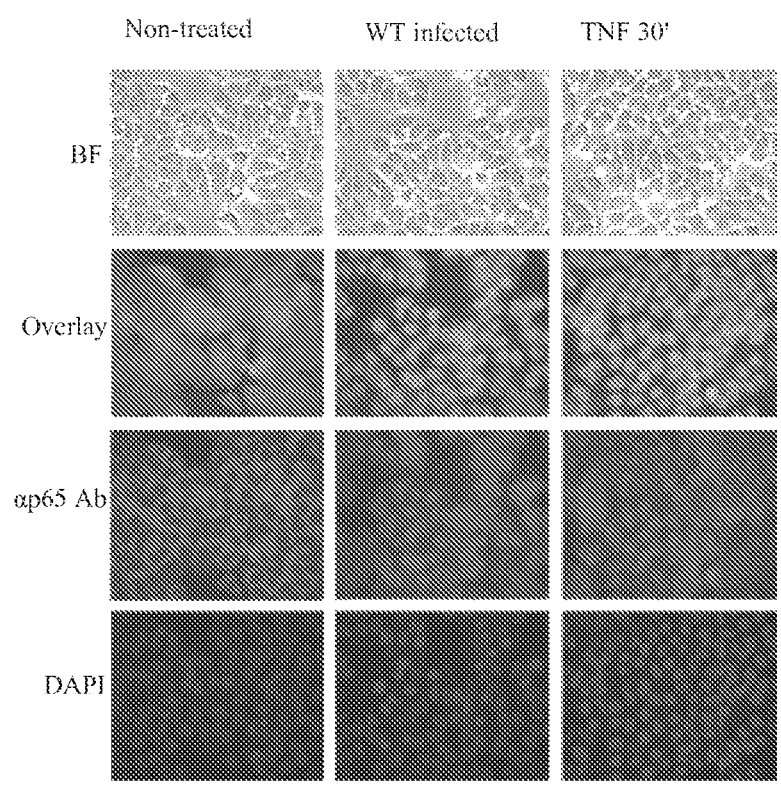
Fig. 1

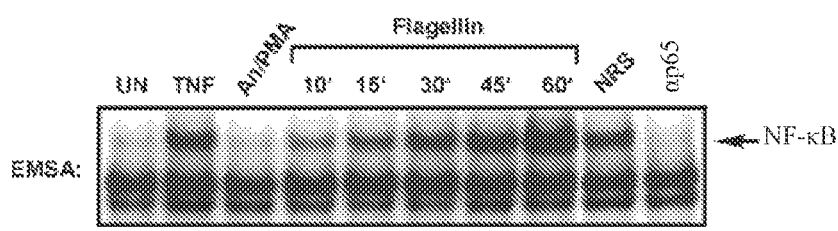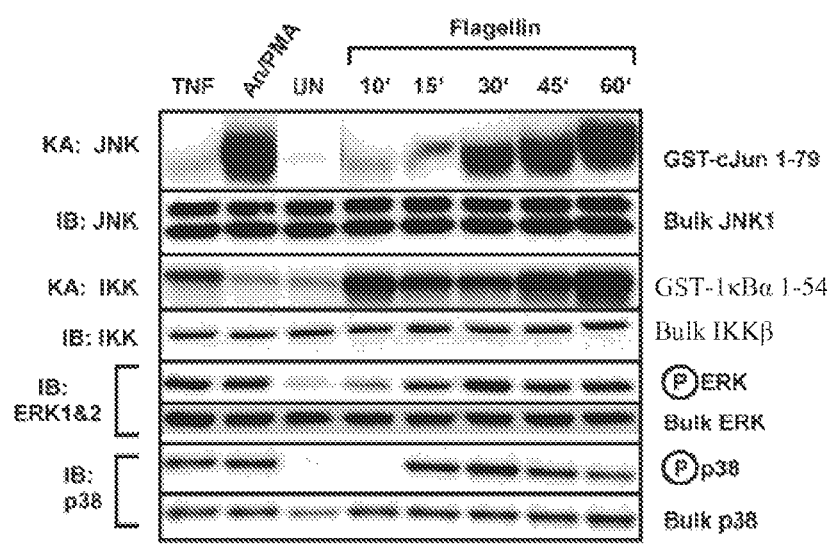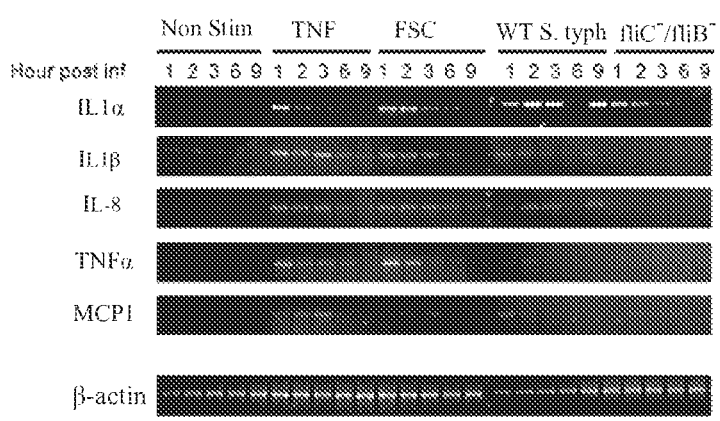
Fig. 6

Fig. 8
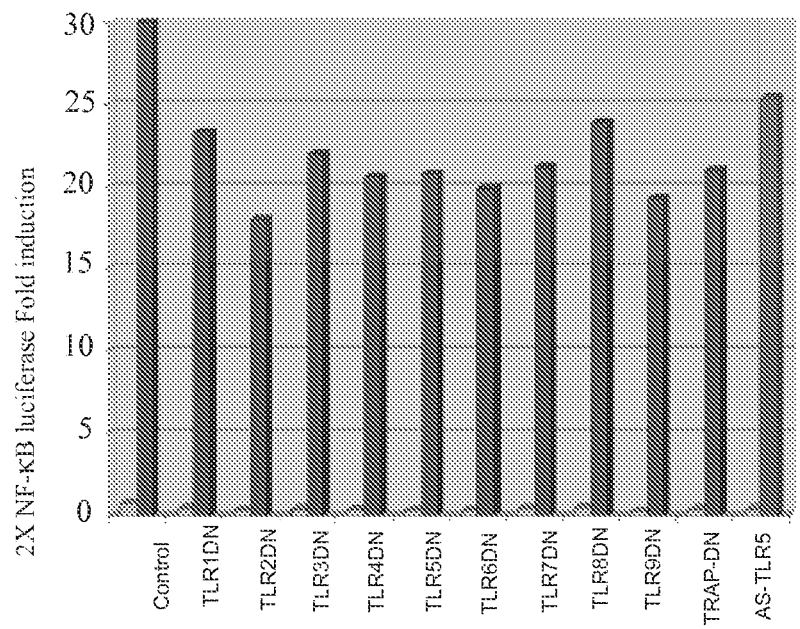
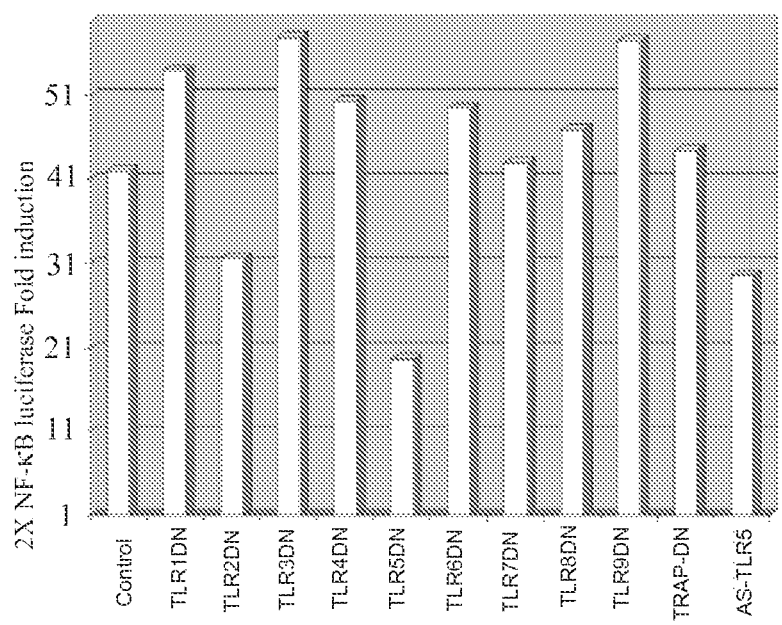

Fig. 10
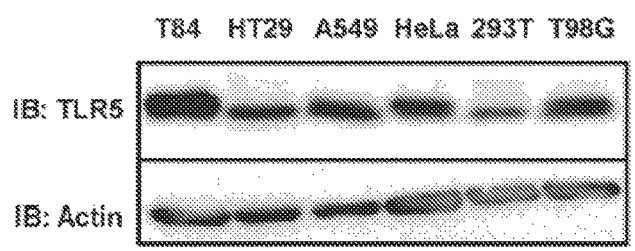
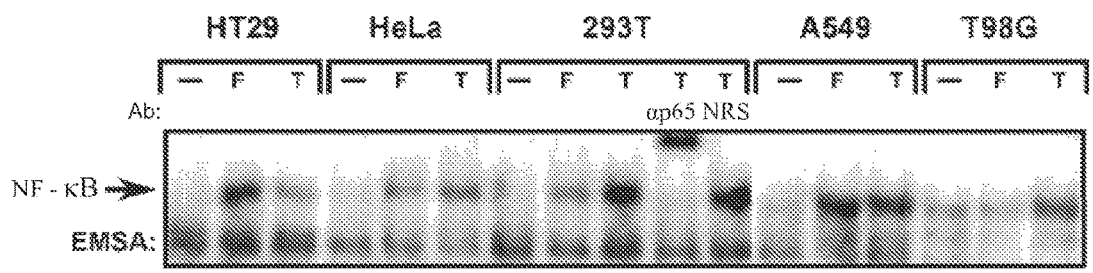

Fig. 15
Small intestine, day 7
 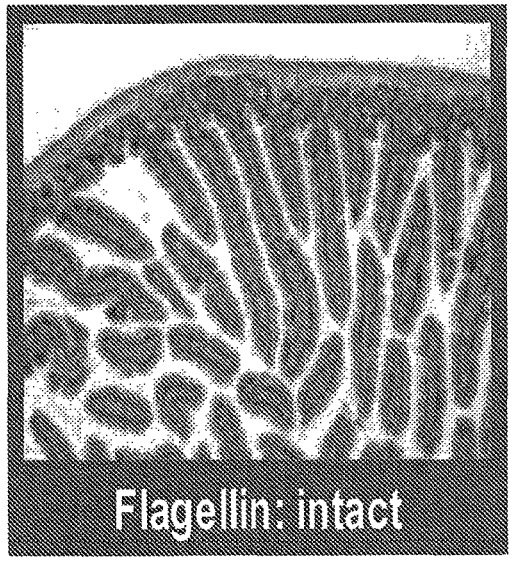

PROTECTION AGAINST STRESS-MEDIATED DAMAGE FROM IONIZING RADIATION

CROSS REFERENCE TO RELATED APPLICATIONS

This application is a continuation of U.S. patent application Ser. No. 15/049,953, filed Feb. 22, 2016 (now U.S. Pat. No. 9,585,939), which is a continuation of U.S. patent application Ser. No. 14/305,709 (now U.S. Pat. No. 9,296,793), filed Jun. 16, 2014, which is a continuation of U.S. patent application Ser. No. 12/617,653 filed Nov. 12, 2009 (now U.S. Pat. No. 8,784,840), which is a divisional of U.S. patent application Ser. No. 11/421,918, filed Jun. 2, 2006 (now U.S. Pat. No. 7,638,485), which is a continuation of International Patent Application No. PCT/US2004/040579, filed Dec. 2, 2004, International Patent Application No. PCT/US2004/040749, filed Dec. 2, 2004, International Patent Application No. PCT/US2004/040750, filed Dec. 2, 2004, and International Patent Application No. PCT/US2004/040753, filed Dec. 2, 2004, each of which claims the benefit of U.S. Provisional Application No. 60/526,460, filed. Dec. 2, 2003, U.S. Provisional Application No. 60/526,461, filed Dec. 2, 2003, U.S. Provisional Application No. 60/526,496, filed Dec. 2, 2003, and U.S. Provisional Application No. 60/526,666, filed Dec. 2, 2003, the contents of which are incorporated herein by reference.

FIELD OF THE INVENTION

This invention relates to the modulation of apoptosis.

BACKGROUND OF THE INVENTION

The progression from normal cells to tumor cells involves a loss of negative mechanisms of growth regulation, including resistance to growth inhibitory stimuli and a lack of dependence on growth factors and hormones. Traditional cancer treatments that are based on radiation or cytotoxic drugs rely on the differences in growth control of normal and malignant cells. Traditional cancer treatments subject cells to severe genotoxic stress. Under these conditions, the majority of normal cells become arrested and therefore saved, while tumor cells continues to divide and die.

However, the nature of conventional cancer treatment strategy is such that normal rapidly dividing or apoptosis-prone tissues are at risk. Damage to these normal rapidly dividing cells causes the well-known side effects of cancer treatment (sensitive tissues: hematopoiesis, small intestine, hair follicles). The natural sensitivity of such tissues is complicated by the fact that cancer cells frequently acquire defects in suicidal (apoptotic) machinery and those therapeutic procedures that cause death in normal sensitive tissues may not be that damaging to cancer cells. Conventional attempts to minimize the side effects of cancer therapies are based on (a) making tumor cells more susceptible to treatment, (b) making cancer therapies more specific for tumor cells, or (c) promoting regeneration of normal tissue after treatment (e.g., erythropoietin, GM-CSF, and KGF).

There continues to be a need for therapeutic agents to mitigate the side effects associated with chemotherapy and radiation therapy in the treatment of cancer. This invention fulfills these needs and provides other related advantages.

SUMMARY OF THE INVENTION

A method of protecting a mammal from a condition that triggers apoptosis is provided. The mammal may be administered a composition comprising an agent that induces NF-kB. The agent may be flagellin or TGFβ, which may be latent TGFβ.

The condition may be radiation exposure. The composition may be administered in combination with a radioprotectant, which may be an antioxidant or a cytokine. The antioxidant may be amifostine or vitamin E. The cytokine may be a stem cell factor.

The condition may also be a constitutively active NF-kB cancer. The condition may also be a cancer treatment, which may be chemotherapy or radiation therapy. The composition may be administered prior to, together with, or after the cancer treatment.

The condition may also be cell aging, radiation, wounding, poisoning, infection or temperature shock.

Also provided is a method of screening for a modulator of apoptosis. A suspected modulator may be added to a cell-based apoptosis system. A control may also be added to the cell-based apoptosis system. The level of apoptosis of the suspected modulator and the control may be compared to identity a modulator of apoptosis. The suspected modulator may be derived from a mammalian parasite. The modulator of apoptosis may be a modulator or NF-kB, TGFβ, or p53. The cell-based apoptosis system may be a NF-kB-, TGFβ-, or p53-activated expression system. The level apoptosis may be the level of NF-kB-, TGFβ-, or p53-activated expression. The parasite species may include, but are not limited to, *Salmonella*, *Mycoplasma*, or *Chlamydia*.

BRIEF DESCRIPTION OF THE DRAWINGS

FIG. 1 demonstrates that *Salmonella* infection leads to NF-κB nuclear localization even in non-infected cells. HT29 cells were grown on glass coverslips and either mock-infected, left untreated, infected with *Salmonella typhimurium*, or treated with TNFα (10 ng/ml). Panel A: HT29 cells were mock-infected or infected at an MOI of 100 with *Salmonella typhimurium* strain SJW1103G which expresses GFP from the ssaH promoter that is only active inside infected host cells. Cells were photographed using bright field microscopy (BF), and immunofluorescence to detect GFP or DAPI staining as indicated. Images were merged (overlay) to reveal cells that were infected. Panel B: HT29 cells were left untreated, infected with *Salmonella typhimurium* strain 1103 or treated with TNFα. NF-κB p65(RelA) localization under various conditions as indicated was monitored by indirect immunofluorescence. Cells were visualized by bright field microscopy (BF), cell nuclei were stained with DAPI and p65(RelA) was visualized with FITC. DAPI staining was falsely colored red to make visualization of the merge (overlay) easier to distinguish.

FIG. 6 demonstrates that purified flagellin activates signaling pathways and proinflammatory gene expression in intestinal epithelial cells mimicking that of a wild-type *Salmonella* infection. HT29 cells were left untreated or treated with TNFα (10 ng/ml) or a cocktail of anisomycin [An] (20 µg/ml)/PMA (12.5 ng/ml) for 10 min, or with flagellin (1 µg/ml) for the indicated times. WCE were prepared and analyzed by EMSA for NF-κB DNA binding activity, immuno-kinase assays (KA) or immunoblot analysis using phospho-specific antibodies for ERK or p38 to detect activation and with kinase-specific antibodies as described in FIG. 5A to detect bulk kinase abundance as indicated. Panel A: EMSA to detect NF-κB DNA binding activity. Panel B: immunoblot and kinase assays to detect IKK, JNK, ERK and p38 kinase activities and protein abundance as in FIG. 5A. Panel C: semi-quantitative RT-PCR of proinflammatory gene expression of non-treated, wild-type and flagellin double mutant *Salmonella typhimurium* infected, TNFα (10 ng/ml) or flagellin (1 mg/ml) stimulated cells. HT29 cells were harvested at the indicated times after the indicated treatments and isolated RNA was used to make first strand cDNA that subsequently used in RT-PCR reactions using gene-specific primers for IL1α, IL1β, IL-8, TNFα, MCP1 and β-actin. β-actin was used as a standard for normalizing expression patterns. Resulting PCR products were fractionated on 2% agarose gels and visualized by ethidium bromide staining.

FIG. 8 demonstrates that TLR5 inhibits flagellin-mediated NF-κB reporter gene activity. HT29 cells were transfected in triplicate in 6-well dishes using the indicated DN-TLR mammalian expression vectors or antisense TLR5 (AS TLR5) (2 µg/well), 2×NF-κB Luc reporter gene (100 ng/well), pRL-TK *Renilla* luciferase for normalization (50 ng/well) adjusted to 4 µg total DNA/well with empty vector pCDNA3.1 DNA. Panel A: Fold-induction of 2× NF-κB Luc reporter gene in non-stimulated cells (light shading) and in TNFα (10 ng/ml) treated cells (dark shading). Lysates were prepared 12 h after stimulation. Results of a representative experiment are shown. Panel B: HT29 cells transfected as in FIG. 8A were treated with flagellin (1 µg/ml) and cell lysates were prepared and analyzed as in FIG. 8A. Results of a representative experiment are shown.

FIG. 10 demonstrates that TLR5 is expressed in numerous cell types and has variable responses to flagellin. Panel A: whole cell extracts were prepared from non-stimulated T84, HT29, A549, HeLa, 293T and T980 cells and fractionated on a 8% SDS-PAGE gel, proteins were transferred to PVDF membrane and probed with anti-TLR5 antibody for immunoblot analysis (IB). Protein loading was examined by probing with anti-actin antibody. Panel B: HT29, A549, HeLa, 293T and T98G cells were left untreated (--), treated with flagellin (F) or TNFα (T) and WCEs were prepared after 45 min and used in EMSA to monitor NF-κB DNA binding activity. Authenticity of the NF-κB bandshift was tested with supershift of the complex with p65(RelA)-specific antibody.

FIG. 15 shows histological sections (HE stained) of small intestinal epithelium of mice that were treated with 15 Gy of gamma radiation with or without i.v. injection of 0.25 mg/kg of flagellin. Complete destruction of crypts and villi in control mouse contrasts with close to normal morphology of tissue from flagellin-treated animal.

DETAILED DESCRIPTION

Figure 2:
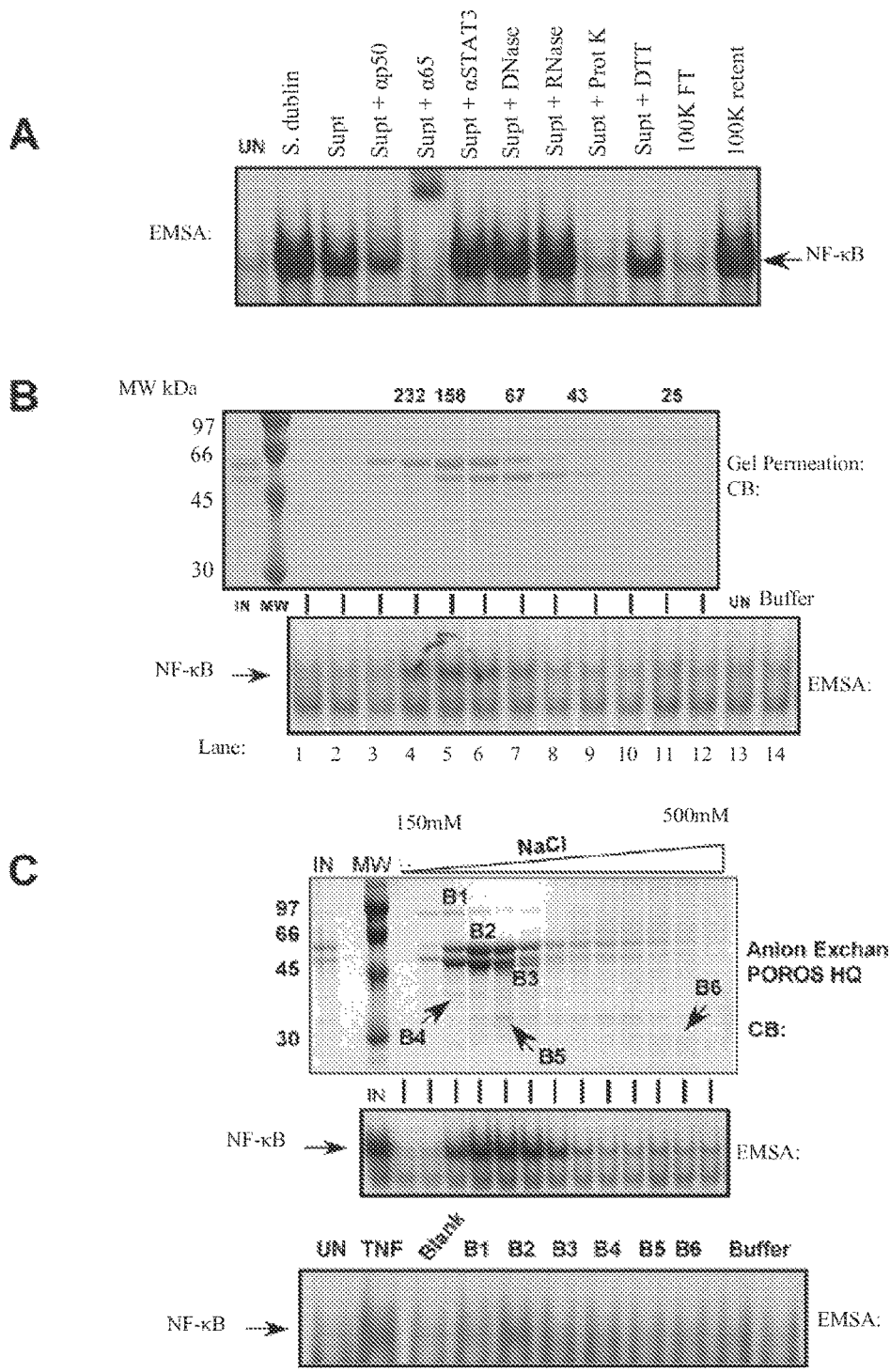
FIG. 2 demonstrates that a protein factor in *Salmonella* culture broth leads to NF-κB activation. Panel A: *Salmonella dublin* culture broth concentrated 100-fold was treated as indicated or infectious bacteria, as indicated was used to challenge HT29 cells. NF-κB DNA binding activity was assayed by EMSA from whole cell extracts prepared 45 min after treatment. Authenticity of the NF-κB DNA:protein complex was determined using p65(RelA)-specific and p50-specific antibody supershifts. Panel B: Concentrated *Salmonella dublin* culture broth (IN) was chromatographed by gel permeation on a Superose 12 column. Eluted protein fractions were analyzed by fractionation on 10% SDS-PAGE and visualized by Coomassie blue (CB) staining. Molecular weight markers for chromatography and on the gels are indicated. Aliquots of each fraction as indicated was used to stimulate HT29 cells and resultant WCEs were analyzed by EMSA for NF-κB DNA binding activity. Panel C: Concentrated *Salmonella dublin* culture broth (IN) was chromatographed by anion exchange chromatography on POROS HQ matrix. Proteins were eluted with an increasing NaCl gradient as indicated and analyzed on 10% SDS-PAGE and visualized by Coomassie blue (CB) staining. Input and aliquots of each fraction as indicated was used to stimulate HT29 cells and resultant WCEs were analyzed by EMSA for NF-κB DNA binding activity. Eluted material corresponding to protein bands B1-B6 and a blank portion of the gel isolated from a duplicate 10% SDS-PAGE gel, along with buffer samples from the beginning and end NaCl buffer gradient were used to stimulate HT29 cells and resultant WCEs were analyzed by EMSA for NF-κB DNA binding activity.

This invention is based on protecting normal cells and tissues from apoptosis caused by stresses including, but not limited to, chemotherapy, radiation therapy and radiation. There are two major mechanisms controlling apoptosis in the cell: the p53 pathway (pro-apoptotic) and the NF-κB pathway (anti-apoptotic). Both pathways are frequently deregulated in tumors: p53 is usually lost, while NF-κB becomes constitutively active. Hence, inhibition of p53 and activation of NF-κB in normal cells may protect them from death caused by stresses, such as cancer treatment, but would not make tumor cells more resistant to treatment because they have these control mechanisms deregulated. This contradicts the conventional view on p53 and NF-κB, which are considered as targets for activation and repression, respectively.

This invention relates to inducing NF-κB activity to protect normal cells from apoptosis. By inducing NF-κB activity in a mammal, normal cells may be protected from apoptosis attributable to cellular stress, which occurs in cancer treatments and hyperthermia; exposure to harmful doses of radiation, for example, workers in nuclear power plants, the defense industry or radiopharmaceutical production, and soldiers; and cell aging. Since NF-κB is constitutively active in many tumor cells, the induction of NF-κB activity may protect normal cells from apoptosis without providing a beneficial effect to tumor cells. Once the normal cells are repaired, NF-κB activity may be restored to normal levels. NF-κB activity may be induced to protect such radiation- and chemotherapy-sensitive tissues as the hematopoietic system (including immune system), the epithelium of the gut, and hair follicles.

Inducers of NF-κB activity may also be used for several other applications. Pathological consequences and death caused by exposure of mammals to a variety of severe conditions including, but not limited to, radiation, wounding, poisoning, infection, aging, and temperature shock, may result from the activity of normal physiological mechanisms of stress response, such as induction of programmed cell death (apoptosis) or release of bioactive proteins, cytokines.

Apoptosis normally functions to "clean" tissues from wounded and genetically damaged cells, while cytokines serve to mobilize the defense system of the organism against the pathogen. However, under conditions of severe injury both stress response mechanisms can by themselves act as causes of death. For example, lethality from radiation may result from massive p53-mediated apoptosis occurring in hematopoietic, immune and digestive systems. Rational pharmacological regulation of NF-κB may increase survival under conditions of severe stress. Control over these factors may allow control of both inflammatory response and the life-death decision of cells from the injured organs.

The protective role of NF-κB is mediated by transcriptional activation of multiple genes coding for: a) anti-apoptotic proteins that block both major apoptotic pathways, b) cytokines and growth factors that induce proliferation and survival of HP and other stem cells, and c) potent ROS-scavenging antioxidant proteins, such as MnSOD (SOD-2). Thus, by temporal activation of NF-κB for radioprotection, it may be possible to achieve not only suppression of apoptosis in cancer patients, but also the ability to reduce the rate of secondary cancer incidence because of simultaneous immunostimulatory effect, which, may be achieved if activation of NF-κB is reached via activation of Toll-like receptors.

Another attractive property of the NF-κB pathway as a target is its activation by numerous natural factors that can be considered as candidate radioprotectants. Among these, are multiple pathogen-associated molecular patterns (PAMPs). PAMPs are molecules that are not found in the host organism, are characteristic for large groups of pathogens, and cannot be easily mutated. They are recognized by Toll-like receptors (TLRs), the key sensor elements of innate immunity. TLRs act as a first warning mechanism of immune system by inducing migration and activation of immune cells directly or through cytokine release. TLRs are type I membrane proteins, known to work as homo- and heterodimers. Upon ligand binding, TLRs recruit MyD88 protein, an indispensable signaling adaptor for most TLRs. The signaling cascade that follows leads to effects including (i) activation of NF-κB pathway, and (ii) activation of MAPKs, including Jun N-terminal kinase (JNK). The activation of the NF-κB pathway by Toll-like receptor ligands makes the ligands attractive as potential radioprotectors. Unlike cytokines, many PAMPs have little effect besides activating TLRs and thus are unlikely to produce side effects. Moreover, many PAMPs are present in humans.

Consistently with their function of immunocyte activation, all TLRs are expressed in spleen and peripheral blood leukocytes, with more TLR-specific patterns of expression in other lymphoid organs and subsets of leukocytes. However, TLRs are also expressed in other tissues and organs of the body, e.g., TLR1 is expressed ubiquitously, TLR5 is also found in GI epithelium and endothelium, while TLRs 2, 6, 7 and 8 are known to be expressed in lung.

1. Definitions

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

As used herein, the terms "administer" when used to describe the dosage of an agent that induces NF-κB activity, means a single dose or multiple doses of the agent.

As used herein, the term "analog", when used in the context of a peptide or polypeptide, means a peptide or polypeptide comprising one or more non-standard amino acids or other structural variations from the conventional set of amino acids.

As used herein, the term "antibody" means an antibody of classes IgG, IgM, IgA, IgD or IgE, or fragments or derivatives thereof, including Fab, F(ab')$_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

As used herein, "apoptosis" refers to a form of cell death that includes progressive contraction of cell volume with the preservation of the integrity of cytoplasmic organelles; condensation of chromatin (i.e., nuclear condensation), as viewed by light or electron microscopy, and/or DNA cleavage into nucleosome-sized fragments, as determined by centrifuged sedimentation assays. Cell death occurs when the membrane integrity of the cell is lost (e.g., membrane blebbing) with engulfment of intact cell fragments ("apoptotic bodies") by phagocytic cells.

As used herein, the term "cancer" means any condition characterized by resistance to apoptotic stimuli.

As used herein, the term "cancer treatment" means any treatment for cancer known in the art including, but not limited to, chemotherapy and radiation therapy.

As used herein, the term "combination with" when used to describe administration of an agent that induces NF-κB activity and an additional treatment means that the agent may be administered prior to, together with, or after the additional treatment, or a combination thereof.

As used herein, the term "derivative", when used in the context of a peptide or polypeptide, means a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives include, but are not limited to, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

As used herein, the term "flagellin" means flagellin from any source including, but not limited to, any bacterial species. The flagellin may be from a species of Salmonella. Also specifically contemplated are fragments, variants, analogs, homologs, or derivatives of said flagellin, and combinations thereof. The various fragments, variants, analogs, homologs or derivatives described herein may be 50%, 55%, 60%, 65%, 70%, 75%, 80%, 85%, 90%, 95%, 97%, 98%, or 99% identical to a wild-type flagellin.

As used herein, the term "fragment", when used in the context of a peptide or polypeptide, means a peptides of from about 8 to about 50 amino acids in length. The fragment may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length.

As used herein, the term "homolog", when used in the context of a peptide or polypeptide, means a peptide or polypeptide sharing a common evolutionary ancestor.

As used herein, the term "latent TGFβ" means a precursor of TGFβ that is not in an active form. A latent TGFβ may be a precursor of TGFβ containing active TGFβ and latency-associated peptide (LAP). A latent TGFβ may also comprise LAP linked to latent TGFβ binding protein. A latent TGFβ may also be the large latent complex. Furthermore, a latent TGFβ may be a latent TGFβ that is modified so that the rate of conversion to active TGFβ or ability to be converted to TGFβ has been reduced. The modified latent TGFβ may be, for example, a TGFβ mutant that prevents or reduces conversion to active TGFβ.

As used herein, the term "TGFβ" means any isoform of active or latent TGFβ including, but not limited to, TGFβ1, TGFβ2, TGFβ3, TGFβ4 or TGFβ5, and combinations thereof. Also specifically contemplated are fragments, variants, analogs, homologs, or derivatives of said TGFβ isoforms, and combinations thereof. The various fragments, variants, analogs, homologs or derivatives described herein may be 50%, 55%, 60%, 65%, 70%, 75%, 80%, 85%, 90%, 95%, 97%, 98%, or 99% identical to a TGFβ isoform.

As used herein, the term "treat" or "treating" when referring to protection of a mammal from a condition, means preventing, suppressing, repressing, or eliminating the condition.

Preventing the condition involves administering a composition of this invention to a mammal prior to onset of the condition. Suppressing the condition involves administering a composition of this invention to a mammal after induction of the condition but before its clinical appearance. Repressing the condition involves administering a composition of this invention to a mammal after clinical appearance of the condition such that the condition is reduced or maintained. Elimination the condition involves administering a composition of this invention to a mammal after clinical appearance of the condition such that the mammal no longer suffers the condition.

As used herein, the term "tumor cell" means any cell characterized by resistance to apoptotic stimuli.

As used herein, the term "variant", when used in the context of a peptide or polypeptide, means a peptide or polypeptide that differs in amino acid sequence by the insertion, deletion, or conservative substitution of amino acids, but retain at least one biological activity. For purposes of this invention, "biological activity" includes, but is not limited to, the ability to be bound by a specific antibody. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ∀2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated herein by reference. Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. Methods of Treatment a. Constitutively Active NF-κB Tumor

This invention relates to a method of treating a mammal suffering from a constitutively active NF-κB cancer comprising administering to the mammal a composition comprising a therapeutically effective amount of an agent that induces NF-κB activity. The agent that induces NF-κB activity may be administered in combination with a cancer treatment.

The agent may be administered simultaneously or metronomically with other anti-cancer treatments such as chemotherapy and radiation therapy. The term "simultaneous" or "simultaneously" as used herein, means that the other anti-cancer treatment and the compound of This invention administered within 48 hours, preferably 24 hours, more preferably 12 hours, yet more preferably 6 hours, and most preferably 3 hours or less, of each other. The term "metronomically" as used herein means the administration of the compounds at times different from the chemotherapy and at certain frequency relative to repeat administration and/or the chemotherapy regiment.

The agent may be administered at any point prior to exposure to the cancer treatment including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to exposure. The agent may be administered at any point after exposure to the cancer treatment including, but not limited to, about 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after exposure.

The cancer treatment may comprise administration of a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-α), etoposide, and teniposide.

Other proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; and Panda (1996) J. Biol. Chem 271:29807-29812.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used include, but are not limited to, hormones and steroids (including synthetic analogs): 17.alpha.-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, hlorotrianisene, hydroxyprogesterone, aminoglutethimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

A variety of cancers may be treated according to this invention including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoictic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma. In a preferred embodiment, this invention is used to treat cancers of gastrointestinal tract.

b. Treatment of Side Effects from Cancer Treatment

This invention also relates to a method of treating a mammal suffering from damage to normal tissue attributable to treatment of a constitutively active NF-κB cancer, comprising administering to the mammal a composition comprising a therapeutically effective amount of an agent that induces NF-κB activity. The agent that induces NF-κB activity may be administered in combination with a cancer treatment described above.

c. Modulation of Cell Aging

This invention also relates to a method of modulating cell aging in a mammal, comprising administering to the mammal a therapeutically effective amount of an agent that induces NF-κB activity. The agent that induces NF-κB activity may be administered in combination with other treatments.

The agent may be administered at any point prior to administration of the other treatment including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to administration. The agent may be administered at any point after administration of the other treatment including, but not limited to, about 1 hr, 2 hr, 3 hr, 4 hr, 6 hr, 8 hr, 10 hr, 12 hr, 14 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after administration.

d. Treatment of Stress

This invention also relates to a method of treating a mammal suffering from damage to normal tissue attributable to stress, comprising administering to the mammal a composition comprising a therapeutically effective amount of an agent that induces NF-κB activity. The agent that induces NF-κB activity may be administered in combination with other treatments. The stress may be attributable to any source including, but not limited to, radiation, wounding, poisoning, infection, and temperature shock.

The composition comprising an inducer of NF-κB may be administered at any point prior to exposure to the stress including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to exposure. The composition comprising an inducer of NF-κB may be administered at any point after exposure to the stress including, but not limited to, about 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after exposure.

e. Radiation

This invention is also related to the protection of cells from the effects of exposure to radiation. Injury and death of normal cells from ionizing radiation is a combination of a direct radiation-induced damage to the exposed cells and an active genetically programmed cell reaction to radiation-induced stress resulting in a suicidal death or apoptosis. Apoptosis plays a key role in massive cell loss occurring in several radiosensitive organs (i.e., hematopoietic and immune systems, epithelium of digestive tract, etc.), the failure of which determines general radiosensitivity of the organism.

Exposure to ionizing radiation (IR) may be short- or long-term, it may be applied as a single or multiple doses, to the whole body or locally. Thus, nuclear accidents or military attacks may involve exposure to a single high dose of whole body irradiation (sometimes followed by a long-term poisoning with radioactive isotopes). The same is true (with strict control of the applied dose) for pretreatment of patients for bone marrow transplantation when it is necessary to prepare hematopoietic organs for donor's bone marrow by "cleaning" them from the host blood precursors. Cancer treatment may involve multiple doses of local irradiation that greatly exceeds lethal dose if it were applied as a total body irradiation. Poisoning or treatment with radioactive isotopes results in a long-term local exposure to radiation of targeted organs (e.g., thyroid gland in the case of inhalation of 125I). Finally, there are many physical forms of ionizing radiation differing significantly in the severity of biological effects.

At the molecular and cellular level, radiation particles are able to produce breakage and cross-linking in the DNA, proteins, cell membranes and other macromolecular structures. Ionizing radiation also induces the secondary damage to the cellular components by giving rise to the free radicals and reactive oxygen species (ROS). Multiple repair systems counteract this damage, such as several DNA repair pathways that restore the integrity and fidelity of the DNA, and antioxidant chemicals and enzymes that scavenge the free radicals and ROS and reduce the oxidized proteins and lipids. Cellular checkpoint systems detect the DNA defects and delay cell cycle progression until damage is repaired or decision to commit cell to growth arrest or programmed cell death (apoptosis) is reached Radiation can cause damage to mammalian organism ranging from mild mutagenic and carcinogenic effects of low doses to almost instant killing by high doses. Overall radiosensitivity of the organism is determined by pathological alterations developed in several sensitive tissues that include hematopoietic system, reproductive system and different epithelia with high rate of cell turnover.

Acute pathological outcome of gamma irradiation leading to death is different for different doses and is determined by the failure of certain organs that define the threshold of organism's sensitivity to each particular dose. Thus, lethality at lower doses occurs from bone marrow aplasia, while moderate doses kill faster by inducing a gastrointestinal (GI) syndrome. Very high doses of radiation can cause almost instant death eliciting neuronal degeneration.

Organisms that survive a period of acute toxicity of radiation can suffer from long-term remote consequences that include radiation-induced carcinogenesis and fibrosis developing in exposed organs (e.g., kidney, liver or lungs) months and years after irradiation.

Cellular DNA is the major target of IR that causes a variety of types of DNA damage (genotoxic stress) by direct and indirect (free radical-based) mechanisms. All organisms maintain DNA repair system capable of effective recovery of radiation-damaged DNA; errors in DNA repair process may lead to mutations.

Tumors are generally more sensitive to gamma radiation and can be treated with multiple local doses that cause relatively low damage to normal tissue. Nevertheless, in some instances, damage of normal tissues is a limiting factor in application of gamma radiation for cancer treatment. The use of gamma-irradiation during cancer therapy by conventional, three-dimensional conformal or even more focused BeamCath delivery has also dose-limiting toxicities caused by cumulative effect of irradiation and inducing the damage of the stem cells of rapidly renewing normal tissues, such as bone marrow and gastrointestinal (GI) tract.

At high doses, radiation-induced lethality is associated with so-called hematopoietic and gastrointestinal radiation syndromes. Hematopoietic syndrome is characterized by loss of hematopoietic cells and their progenitors making it impossible to regenerate blood and lymphoid system. The death usually occurs as a consequence of infection (result of immunosuppression), hemorrhage and/or anemia. GI syndrome is caused by massive cell death in the intestinal epithelium, predominantly in the small intestine, followed by disintegration of intestinal wall and death from bacteriemia and sepsis. Hematopoietic syndrome usually prevails at the lower doses of radiation and leads to the more delayed death than GI syndrome.

In the past, radioprotectants were typically antioxidants—both synthetic and natural. More recently, cytokines and growth factors have been added to the list of radioprotectants; the mechanism of their radioprotection is considered to be a result of facilitating effect on regeneration of sensitive tissues. There is no clear functional distinction between both groups of radioprotectants, however, since some cytokines induce the expression of the cellular antioxidant proteins, such as manganese superoxide dismutase (MnSOD) and metallothionein.

The measure of protection for a particular agent is expressed by dose modification factor (DMF or DRF). DMF is determined by irradiating the radioprotector treated subject and untreated control subjects with a range of radiation doses and then comparing the survival or some other endpoints. DMF is commonly calculated for 30-day survival (LD50/30 drug-treated divided by LD50/30 vehicle-treated) and quantifies the protection of the hematopoietic system. In order to estimate gastrointestinal system protection, LD50 and DMF are calculated for 6- or 7-day survival. DMF values provided herein are 30-day unless indicated otherwise.

Inducers of NF-κB possess strong pro-survival activity at the cellular level and on the organism as a whole. In response to super-lethal doses of radiation, inducers of NF-κB inhibit both gastrointestinal and hematopoietic syndromes, which are the major causes of death from acute radiation exposure. As a result of these properties, inducers of NF-κB may be used to treat the effects of natural radiation events and nuclear accidents. Moreover, since inducers of NF-κB acts through mechanisms different from all presently known radioprotectants, they can be used in combination with other radioprotectants, thereby, dramatically increasing the scale of protection from ionizing radiation.

As opposed to conventional radioprotective agents (e.g., scavengers of free radicals), anti-apoptotic agents may not reduce primary radiation-mediated damage but may act against secondary events involving active cell reaction on primary damage, therefore complementing the existing lines of defense. Pifithrin-alpha, a pharmacological inhibitor of p53 (a key mediator of radiation response in mammalian cells), is an example of this new class of radioprotectants. However, the activity of p53 inhibitors is limited to protection of the hematopoietic system and has no protective effect in digestive tract (gastrointestinal syndrome), therefore, reducing therapeutic value of the e compounds. Anti-apoptotic pharmaceuticals with broader range of activity are desperately needed.

Inducers of NF-κB may be used as a radioprotective agent to extend the range of tolerable radiation doses by increasing radioresistance of human organism beyond the levels achievable by currently available measures (shielding and application of existing bioprotective agents) and drastically increase the chances of crew survival in case of onboard nuclear accidents or large-scale solar particle events. With an approximate DMF (30-day survival) greater than 1.5, the NF-κB inducer flagellin is more effective than any currently reported natural compound.

Inducers of NF-κB are also useful for treating irreplaceable cell loss caused by low-dose irradiation, for example, in the central nervous system and reproductive organs. Inducers of NF-κB may also be used during cancer chemotherapy to treat the side effects associated with chemotherapy, including alopecia.

In one embodiment, a mammal is treated for exposure to radiation, comprising administering to the mammal a composition comprising a therapeutically effective amount of a composition comprising an inducer of NF-κB. The composition comprising an inducer of NF-κB may be administered in combination with one or more radioprotectants. The one or more radioprotectants may be any agent that treats the effects of radiation exposure including, but not limited to, antioxidants, free radical scavengers and cytokines.

Inducers of NF-κB may inhibit radiation-induced programmed cell death in response to damage in DNA and other cellular structures; however, inducers of NF-κB may not deal with damage at the cellular and may not prevent mutations. Free radicals and reactive oxygen species (ROS) are the major cause of mutations and other intracellular damage. Antioxidants and free radical scavengers are effective at preventing damage by free radicals. The combination of an inducer of NF-κB and an antioxidant or free radical scavenger may result in less extensive injury, higher survival, and improved health for mammal exposed to radiation. Antioxidants and free radical scavengers that may be used in the practice of the invention include, but are not limited to, thiols, such as cysteine, cysteamine, glutathione and bilirubin; amifostine (WR-2721); vitamin A; vitamin C; vitamin E; and flavonoids such as Indian holy basil (*Ocimum sanctum*), orientin and vicenin.

Inducers of NF-κB may also be administered in combination with a number of cytokines and growth factors that confer radioprotection by replenishing and/or protecting the radiosensitive stem cell populations. Radioprotection with minimal side effects may be achieved by the use of stem cell factor (SCF, c-kit ligand), Flt-3 ligand, and interleukin-1 fragment IL-1b-rd. Protection may be achieved through induction of proliferation of stem cells (all mentioned cytokines), and prevention of their apoptosis (SCF). The treatment allows accumulation of leukocytes and their precursors prior to irradiation thus enabling quicker reconstitution of the immune system after irradiation. SCF efficiently rescues lethally irradiated mice with DMF in range 1.3-1.35 and is also effective against gastrointestinal syndrome. Flt-3 ligand also provides strong protection in mice (70-80% 30-day survival at LD100/30, equivalent to DMF>1.2) and rabbits (15, 16).

Several factors, while not cytokines by nature, stimulate the proliferation of the immunocytes and may be used in combination with inducers of NF-κB. 5-AED (5-androstenediol) is a steroid that stimulates the expression of cytokines and increases resistance to bacterial and viral infections. A subcutaneous injection of 5-AED in mice 24 h before irradiation improved survival with DMF=1.26. Synthetic compounds, such as ammonium tri-chloro(dioxoethylene-O,O'—) tellurate (AS-101), may also be used to induce secretion of numerous cytokines and for combination with inducers of NF-κB.

Growth factors and cytokines may also be used to provide protection against the gastrointestinal syndrome. Keratinocyte growth factor (KGF) promotes proliferation and differentiation in the intestinal mucosa, and increases the post-irradiation cell survival in the intestinal crypts. Hematopoietic cytokine and radioprotectant SCF may also increase intestinal stem cell survival and associated short-term organism survival.

Inducers of NF-κB may offer protection against both gastrointestinal (GI) and hematopoietic syndromes. Since mice exposed to 15 Gy of whole-body lethal irradiation died mostly from GI syndrome, a composition comprising an inducer of NF-κB and one or more inhibitors of GI syndrome may be more effective. Inhibitors of GI syndrome that may be used in the practice of the invention include, but are not limited to, cytokines such as SCF and KGF.

The composition comprising an inducer of NF-κB may be administered at any point prior to exposure to radiation including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to exposure. The composition comprising an inducer of NF-κB may be administered at any point after exposure to radiation including, but not limited to, about 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after exposure to radiation.

3. Agent

This invention also relates to an agent that induces NF-κB activity. The agent may be an artificially synthesized compound or a naturally occurring compound. The agent may be a low molecular weight compound, polypeptide or peptide, or a fragment, analog, homolog, variant or derivative thereof.

The agent may also be an NF-κB inducing cytokine including, but not limited to, IL2, IL6, TNF and TGFβ. The agent may also be a prostaglandin. The agent may also be a growth factor including, but not limited to, KGF and PDGF. The agent may also be an antibody that induces NF-κB activity.

a. Flagellin

In one embodiment, the agent is flagellin, which may be from a bacteria including, but not limited to, a species of *Salmonella*, such as *S. typhimurium*. As shown in the Examples below, flagellin possesses strong pro-survival activity at the cellular level and on the organism as a whole.

Figure 19:
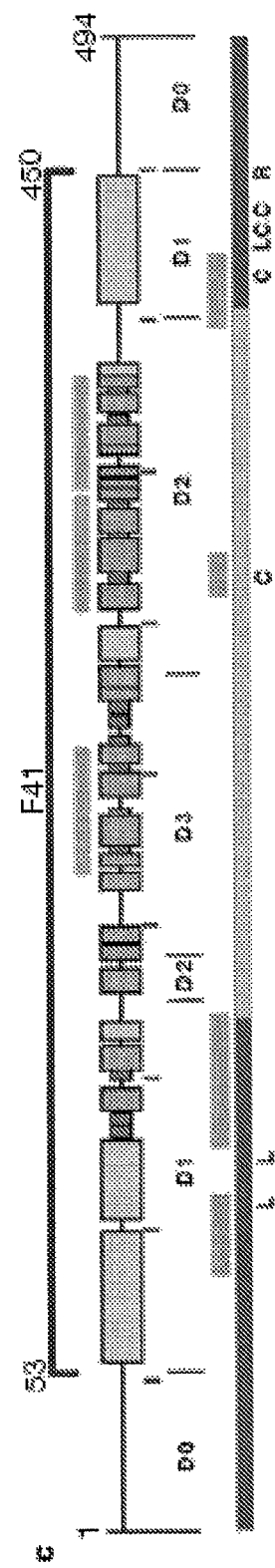
FIG. 19 shows the domain structure of bacterial flagellin. The Cα backbone trace, hydrophobic core distribution and structural information of F41. Four distinct hydrophobic cores that deÆne domains D1, D2a, D2b and D3. All the hydrophobic side-chain atoms are displayed with the Cα backbone. Side-chain atoms are color coded: Ala, yellow; Leu, Ile or Val, orange; Phe and Tyr, purple (carbon atoms) and red (oxygen atoms). c, Position and region of various structural features in the amino-acid sequence of flagellin. Shown are, from top to bottom: the F41 fragment in blue; three b-folium folds in brown; the secondary structure distribution with a-helix in yellow, b-structure in green, and b-turn in purple; tic mark at every 50th residue in blue; domains D0, D1, D2 and D3; the axial subunit contact region within the proto-element in cyan; the well-conserved amino-acid sequence in red and variable region in violet; point mutations in F41 that produce the elements of different supercoils. Letters at the bottom indicate the morphology of mutant elements: L (D107E, R124A, R124S, G426A), L-type straight; R (A449V), R-type straight; C (D313Y, A414V, A427V, N433D), curly33. (Samatey et al, Nature 2001).

A fragment, variant, analog, homolog, or derivative of an inducer of NF-κB, such as flagellin, with beneficial properties may be obtained by rational-based design based on the domain structure of flagellin. The domain structure of *Salmonella* flagellin is described in the literature (FIG. 19). Flagellin has conserved domains (D1 and D2) at the N terminus and C terminus and a middle hypervariable domain (D3) (Samatey, et al 2001, Eaves-Pyles T, et al 2001a). Results with a recombinant protein containing the amino D1 and D2 and carboxyl D1 and D2 separated by an *Escherichia coli* hinge (ND 1-2/ECH/CD2) indicate that D1 and D2 are bioactive when coupled to an ECH element. This chimera, but not the hinge alone, induced $I_\kappa B_\alpha$ degradation, NF-κB activation, and NO and IL-8 production in two intestinal epithelial cell lines. The non-conserved D3 domain is on the surface of the flagellar filament and contains the major antigenic epitopes. The potent proinflammatory activity of flagellin may reside in the highly conserved N and C D1 and D2 regions.

b. Parasitic Inducers of NF-κB

The properties of flagellin suggest that additional modulators of NF-κB may be found in parasites. There are a number of parasites that depend on the repression of apoptosis since they cannot survive without the cells of the host. These organisms may have adapted for effective persistence in the host organism by secreting anti-apoptotic factors. Like advanced tumors, these organisms secrete factors may be capable of increasing their own survival and resolving their conflict with the stress response defensive mechanism of the host.

Anti-apoptotic factors from parasitic or symbiotic organisms have passed through millions of years of adaptation to minimize harm on the host organism that would affect viability. As a result, these factors may require little, if any, additional modifications and may be used directly as they are or with minimal modifications. The factors may be useful to treat stress-mediated apoptosis, such as side effects associated with chemo- and radiation therapy.

This invention is also related to methods for screening parasites for identifying modulators of NF-κB. The candidate modulators may be from parasites of humans or non-human primates. The parasites are preferably extracellular parasites of the host. The parasites may also be symbionts. Parasites from which modulators of This invention may be isolated include, but are not limited to, *Mycoplasma, Chlamydia* and *Salmonella*. These modulators may be identified using the screening methods described herein, as well as by biochemical and genetic selection approaches, in vitro testing, cell death protecting agents, and in vivo.

4. Composition

This invention also relates to a composition comprising a therapeutically effective amount of an inducer of NF-κB. The composition may be a pharmaceutical composition, which may be produced using methods well known in the art. As described above, the composition comprising an inducer of NF-κB may be administered to a mammal for the treatment of conditions associated with apoptosis including, but not limited to, exposure to radiation, side effect from cancer treatments, stress and cell aging. The composition may also comprise additional agents including, but not limited to, a radioprotectant or a chemotherapeutic drug.

a. Administration

Compositions of this invention may be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. For veterinary use, the composition may be administered as a suitably acceptable formulation in accordance with normal veterinary practice. The veterinarian can readily determine the dosing regimen and route of administration that is most appropriate for a particular animal.

b. Formulation

Compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions of this invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or nonaqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

c. Dosage

A therapeutically effective amount of the agent required for use in therapy varies with the nature of the condition being treated, the length of time that induction of NF-κB activity is desired, and the age and the condition of the patient, and is ultimately determined by the attendant physician. In general, however, doses employed for adult human treatment typically are in the range of 0.001 mg/kg to about 200 mg/kg per day. The dose may be about 1 µg/kg to about 100 µg/kg per day. The desired dose may be conveniently administered in a single dose, or as multiple doses administered at appropriate intervals, for example as two, three, four or more subdoses per day. Multiple doses often are desired, or required, because NF-κB activity in normal cells may be decreased once the agent is no longer administered.

The dosage of an inducer of NF-κB may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg or 1 mg/kg.

5. Screening Methods

This invention also relates to methods of identifying agents that induce NF-κB activity. An agent that induces NF-κB activity may be identified by a method comprising adding a suspected inducer of NF-κB activity to an NF-κB activated expression system, comparing the level of NF-κB activated expression to a control, whereby an inducer of NF-κB activity is identified by the ability to increase the level of NF-κB activated expression system.

Candidate agents may be present within a library (i.e., a collection of compounds). Such agents may, for example, be encoded by DNA molecules within an expression library. Candidate agent be present in conditioned media or in cell extracts. Other such agents include compounds known in the art as "small molecules," which have molecular weights less than $10^5$ daltons, preferably less than $10^4$ daltons and still more preferably less than $10^3$ daltons. Such candidate agents may be provided as members of a combinatorial library, which includes synthetic agents (e.g., peptides) prepared according to multiple predetermined chemical reactions. Those having ordinary skill in the art will appreciate that a diverse assortment of such libraries may be prepared according to established procedures, and members of a library of candidate agents can be simultaneously or sequentially screened as described herein.

The screening methods may be performed in a variety of formats, including in vitro, cell-based and in vive assays. Any cells may be used with cell-based assays. Preferably, cells for use with this invention include mammalian cells, more preferably human and non-human primate cells. Cell-base screening may be performed using genetically modified tumor cells expressing surrogate markers for activation of NF-κB. Such markers include, but are not limited to, bacterial beta-galactosidase, luciferase and enhanced green fluorescent protein (EGFP). The amount of expression of the surrogate marker may be measured using techniques standard in the art including, but not limited to, colorimetery, luminometery and fluorimetery.

The conditions under which a suspected modulator is added to a cell, such as by mixing, are conditions in which the cell can undergo apoptosis or signaling if essentially no other regulatory compounds are present that would interfere with apoptosis or signaling. Effective conditions include, but are not limited to, appropriate medium, temperature, pH and oxygen conditions that permit cell growth. An appropriate medium is typically a solid or liquid medium comprising growth factors and assimilable carbon, nitrogen and phosphate sources, as well as appropriate salts, minerals, metals and other nutrients, such as vitamins, and includes an effective medium in which the cell can be cultured such that the cell can exhibit apoptosis or signaling. For example, for a mammalian cell, the media may comprise Dulbecco's modified Eagle's medium containing 10% fetal calf serum.

Cells may be cultured in a variety of containers including, but not limited to tissue culture flasks, test tubes, microtiter dishes, and petri plates. Culturing is carried out at a temperature, pH and carbon dioxide content appropriate for the cell. Such culturing conditions are also within the skill in the art.

Methods for adding a suspected modulator to the cell include electroporation, microinjection, cellular expression (i.e., using an expression system including naked nucleic acid molecules, recombinant virus, retrovirus expression vectors and adenovirus expression), use of ion pairing agents and use of detergents for cell permeabilization.

This invention has multiple aspects, illustrated by the following non-limiting examples.

Example 1

P53 Deficiency Accelerated Development of GI Syndrome in Mice

Figure 11:
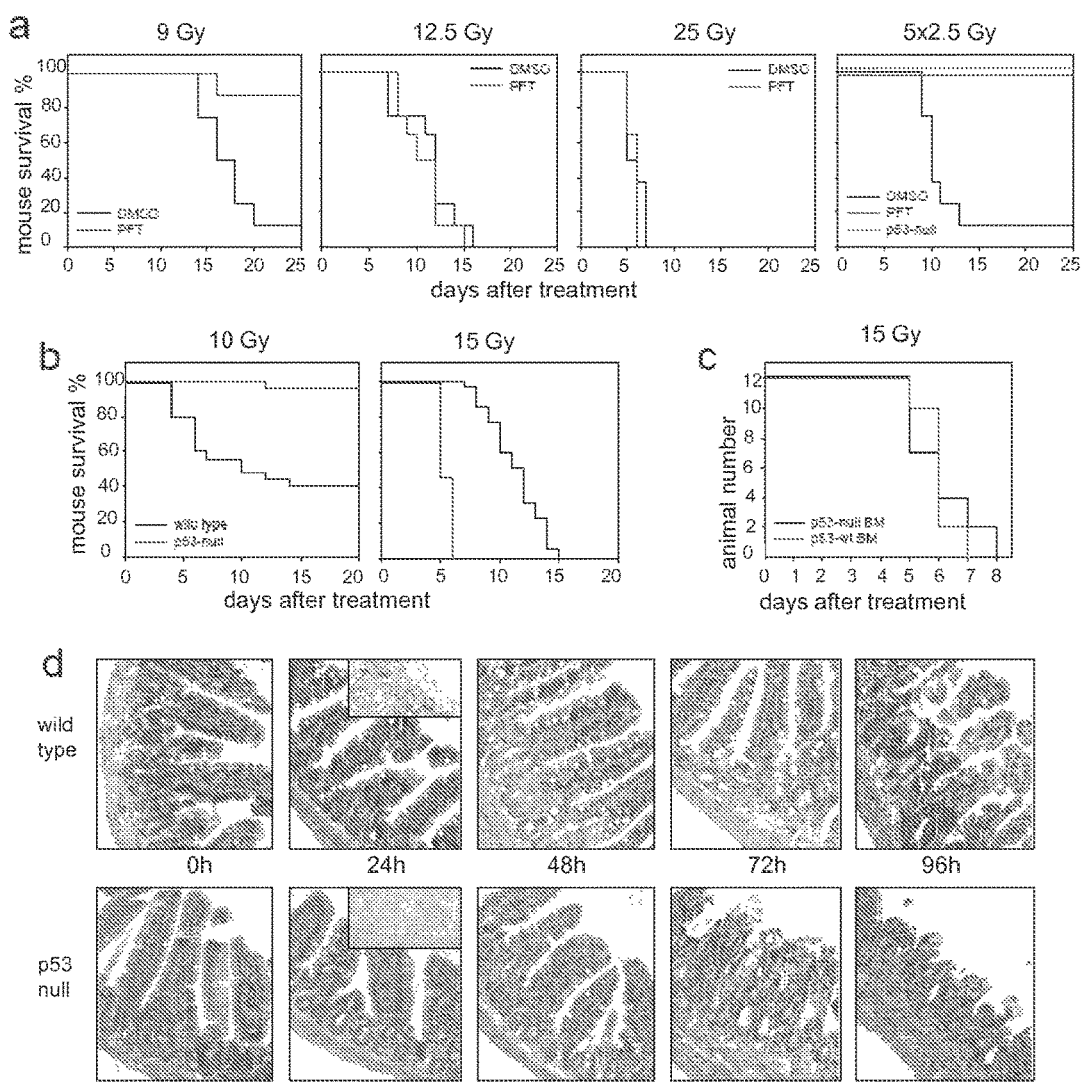
FIG. 11 demonstrates that p53 deficiency accelerated development of GI syndrome in mice. Panel A: I.P. injection of PFTα (10 mg/kg) protects C57Bl/6J mice (if not indicated otherwise, here and below 6-8 weeks old males were used) from a single 9 Gy dose of gamma radiation and a fractioned cumulative radiation dose 12.5 Gy (5×2.5 Gy). PFTα has no effect on survival of mice treated with single 12.5 and 25 Gy doses of IR: (results of representative experiments are shown; Shepherd 4000 Ci Cesium 137 source at a dose rate of 4 Gy per minute was used). Panel B: Wild-type and p53-null C57Bl/6J mice differ in their relative sensitivity to low (10 Gy) and high (15Gy) doses of gamma radiation: wild-type mice were more sensitive to 10 Gy but more resistant to 15 Gy as compared to p53-null mice. Panel C: Mice treated with 11 Gy of total body gamma irradiation were injected 12 h later with $1.5 \times 10^7$ bone marrow cells from wild type or p53-null syngeneic C57Bl/6J mice. (This dose causes 100% lethality in nonreconstituted controls group of mice). Two months later, after complete recovery of hematopoiesis, animals were treated with 15 Gy of total body gamma radiation and showed no difference in death rates between the two groups differing in the p53 status of their bone marrow. Panel D: Comparison of dynamics of injury to small intestines of wild-type and p53-null mice at the indicated time points after 15 Gy of gamma radiation indicates accelerated damage in p53-null mice (haematoxylin-eosin stained paraffin sections; magnification×125). 24 h panels include images of TUNEL staining if sections of crypts: massive apoptosis is evident in wild type but not in p53-deficient epithelium.
Figure 12:
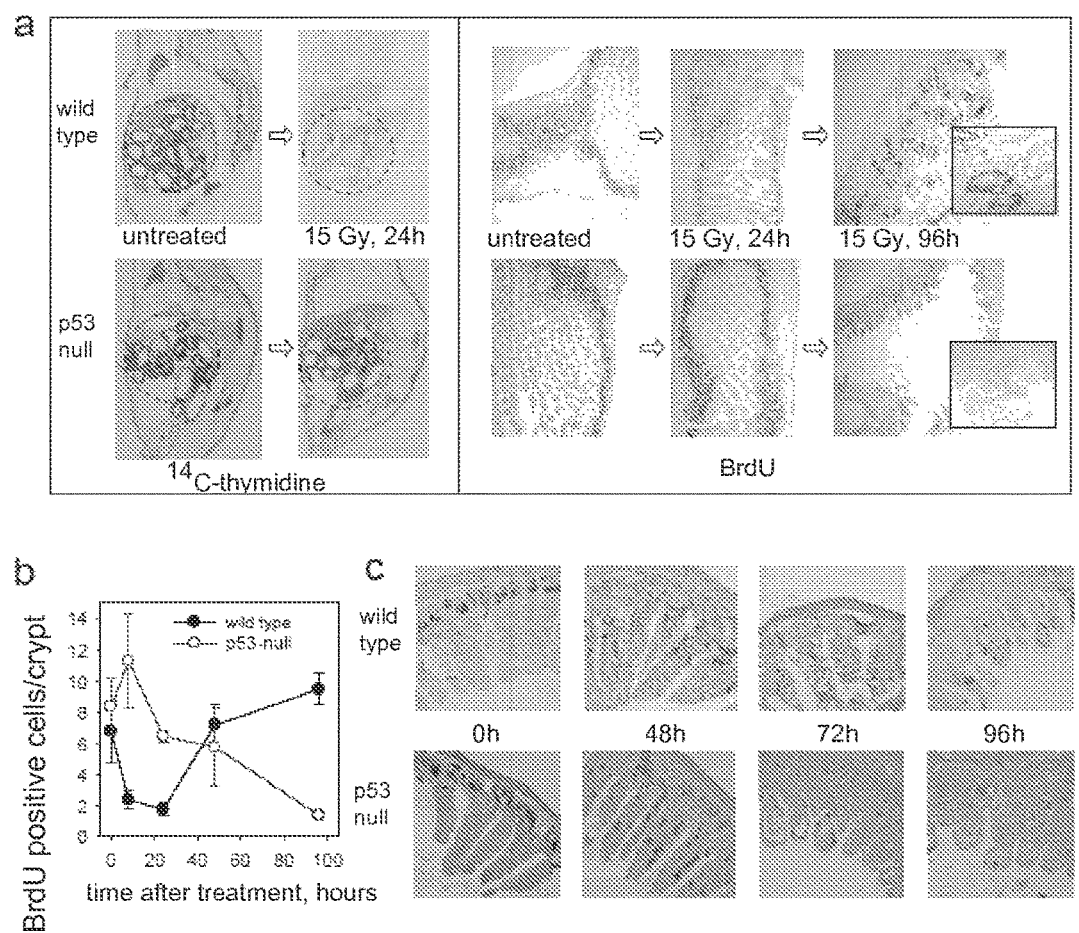
FIG. 12 demonstrates the dynamics of cell proliferation and survival in small intestine of wild type and p53-null mice. Panel A: Comparison of proliferation rates in intestines of wild-type and p53 null mice after treatment with IR. (Left) Autoradiographs of whole-body sections (1.7× magnification) of 4-week-old wild-type and p53 null mice injected intraperitoneally with $^{14}$C-thymidine (10 μCi per animal) treated or untreated with 15 Gy of gamma radiation (Westphal et al 1997). Arrows point at intestines. (Right) Comparison of BrdU incorporation in small intestine of wild-type and p53-null mice at different time points after 15 Gy of gamma radiation. BrdU (50 mg/kg) was injected 2 h before sacrificing mice and immunostaining was done as previously described (Watson & Pritchard 2000). Fragments of 96 h panels are shown at higher magnification (×400). Panel B: Comparison of the number of BrdU positive cells/crypt in small intestine of wild-type and p53-null mice at different time points after 15 Gy of gamma radiation. Three animals were analyzed for each time point, five ileum cross sections were prepared from each animal and analyzed microscopically to estimate the number of crypts and villi. Numbers of BrdU-positive cells in the crypts were counted in 5 random fields under 200× magnification (100-30 crypts) and the average number of BrdU-positive cells was plotted. Panel C: Tracing the number and position of BrdU-labeled cells in small intestine of wild type and p53-null mice during different time points after 15 Gy of gamma radiation. BrdU was injected 30 min. before irradiation and mice were sacrificed at the indicated time points. Accelerated migration from crypts to villi followed by rapid elimination of labeled cells was observed in p53-null mice.

Primary cause of death from ionizing radiation (IR) of mammals depends on the radiation dose. At doses of up to 9-10 Gy, mice die 12-20 days later, primarily from lethal bone marrow depletion-hematopoietic (HP) syndrome. At this dose, irradiated mice can be rescued from lethality by bone marrow transplantation. Animals that received >15 Gy die between 7-12 days after treatment (before hematopoietic syndrome could kill them) from complications of damage to the small intestine-gastrointestinal (GI) syndrome (Gudkov & Komarova 2003). In both cases of HP and GI syndromes, lethal damage of tissues starts from massive p53 dependent apoptosis (Potten 1992, Merritt 1994, Cui et al 1995, Potten et al 1994), the observation that allowed us earlier to suggest that p53 could be a determinant of radiation-induced death. Consistently, p53-deficient mice are resistant to doses of radiation that kill through HP syndrome (Westphal et al 1997, Komarov et al 1999), and lethality of wild type animals receiving 6-11 Gy of gamma radiation can be reduced by temporary pharmacological inhibition of p53 by small molecule p53 inhibitor pifithrin-alpha (PFT) (Komarov et al 1999). Definition of p53 as a factor sensitizing tissues to genotoxic stress was further strengthened by demonstrating the p53 dependence of hair loss (alopecia) occurring as a result of experimental chemotherapy or radiation (Botchkarev et al 2000). Hence, based on previous observations, one could expect that p53 continues to play an important role in development of lethal GI syndrome after higher doses of IR. Surprisingly, p53-deficiency sensitizes mice to higher doses of IR causing lethal gastro-intestinal syndrome (FIG. 11). Continuous cell proliferation in the crypts of p53-deficient epithelium after IR correlates with accelerated death of damaged cells of crypt and rapid destruction of villi. p53 prolongs survival by inducing growth arrest in the crypts of small intestine thereby preserving integrity of the guts (FIG. 12). Thus, proapoptotic function of p53 promotes hematopoietic syndrome while its growth arrest function delays development of gastro-intestinal syndrome.

The dynamics of cell population in the small intestine has been analyzed in great detail. Cell proliferation in epithelia of the guts is limited to the crypts where stem cells and early proliferating progenitors are located. After a couple of cell divisions, already differentiated descendants of crypt stem cells move up the villi to be shed at the villar tip. In the small intestine of the mouse, the entire "trip" of the cell (the proliferative compartment to the tip of the villus) normally takes between 3 and 5 days (Potten 1992, Potten et al 1997, Booth et al 2002, Somosy et al 2002). Although reaction of the small intestine to gamma radiation has been well examined at a pathomorphological level, it still remains unclear what is the exact cause of GI lethality, including the primary event. Death may occur as a direct consequence of the damage of epithelial crypt cells and followed denudation of villi leading to fluid and electrolyte imbalance, bacteremia and endotoxemia. Besides inflammation and stromal responses, endothelial dysfunctions seem to be the important factors contributing to lethality (Potten et al 1997, Somosy et al 2002). In summary, pharmacological suppression of p53 that was shown to be so effective as a method of protection from IR-induced HP syndrome, is useless (if not detrimental) against GI syndrome. Therefore, it is necessary to develop alternative approaches to radioprotection of epithelium of small intestine that will rely on another mechanism, such as, for example, activation of NF-κB and subsequent inhibition of cell death.

Example 2

Salmonella Infection Activates NF-κB

Salmonella infection leads to potent IKK and NF-κB activation and activation of the proinflammatory gene program (Elewaut et al 1999). Previous studies suggest that about 30-40% of intestinal epithelial cells are infected during a typical Salmonella infection in cultured intestinal epithelial cells (Valdivia et al 1996). We wished to address the question of how bacterial infection of about 30% of the host cells could give rise to NF-κB DNA binding activity equivalent to activation of NF-κB in nearly all of the host cells as TNFα treatment does.

To examine this phenomenon in detail, HT29 cells were either mock-infected or infected at a MOI of 50 for one hour with wild-type S. typhimurium that had been transformed with the plasmid pFM10.1 that encodes green fluorescent protein (GFP) under the control of the Salmonella ssaH promoter and only functions once the bacteria has invaded the host cell (Valdivia et al. 1997). Cells that were invaded by Salmonella were detected by direct fluorescence microscopy of GFP expression. p65(RelA) localization was monitored by indirect immunofluorescence of rabbit anti-p65 antibody detected with FITC-conjugated donkey anti-rabbit antibody. DAPI was used to stain nuclei.

As can be seen in FIG. 1A, GFP expression occurs in about thirty to forty percent of the cells. We next examined the localization of the NF-κB subunit p65 (RelA) in non-treated (mock-infected), Salmonella infected or TNFα (10 ng/ml) stimulated cells. P65 (RelA) was localized to the cytoplasm in non-treated cells, whereas p65 (RelA) was localized to the nucleus in Salmonella infected cells or in TNFα treated cells (FIG. 1B). These results demonstrate that Salmonella infection activates NF-κB in virtually all of the cells even though only a minority of them become infected.

Example 3

Flagellin Activates NF-κB

Since Salmonella infection of intestinal epithelial cells in culture led to only roughly 30% infection but activation of NF-κB in nearly all of the cells, we anticipated that NF-κB activation was in response to host cell recognition of bacteria structural components or products produced by the bacteria and not by the invasion process. Invasion itself has been demonstrated not to be required for activation of the proinflammatory gene program as had previously been thought (16). To investigate this possibility sterile-filtered S. dublin culture broth left either untreated or boiled for twenty minutes was used to challenge HT29 intestinal epithelial cells and NF-κB DNA binding activity was monitored by electromobility shift assays (EMSAs) of whole cell extracts (WCE) prepared forty-five minutes after exposure (3, 40). Potent activation of NF-κB in response to the broth under both conditions was observed indicating the activating factor was heat-stable.

The native sterile-filtered concentrated broth was subsequently treated with DNase, RNase, proteinase K or crudely size fractionated on 100 kDa centricon filters. The variously treated broths were then used to challenge HT29 intestinal epithelial cells and WCEs were prepared after forty-five minutes and NF-κB DNA binding activity was analyzed by EMSA (FIG. 2A). Direct infection of HT29 cells by *S. typhimurium* 1103 or exposure to the culture broths (supt), as indicated, induced NF-κB DNA binding activity, while the activity-inducing factor was found to be sensitive to protease digestion and was retained by a 100 kDa filter (FIG. 2A). To further determine the identity of the NF-κB inducing activity, sterile-filtered concentrated broth culture was fractionated by Superose 12 gel permeation chromatography (FIG. 2B) and by anion exchange chromatography (FIG. 2C). Aliquots of chromatography fractions were assayed for their ability to activate NF-κB in HT29 cells and analyzed by EMSA. As can be seen from the Coomassie blue stained gel (FIG. 2B, top panel), increased NF-κB DNA binding activity (FIG. 2B, lower panel lanes 4-6) corresponded to the increased abundance of an approximately 55 kDa protein. Anion exchange chromatography on POROS HQ matrix and elution of bound proteins with an increasing salt gradient as indicated (FIG. 2C) demonstrated that NF-κB DNA binding-inducing activity corresponded to chromatographic fractions containing an increased abundance of the 55 kDa protein (FIG. 2C top panel, and data not shown). Eluted fractions observed in FIG. 2C were concentrated and fractionated on preparative 12% SDS-PAGE gels and bands corresponding to B1-B6 were cut from the gels and the proteins eluted, precipitated, renatured, and used to stimulate HT29 cells. Whole cell extracts from these cells were assayed for NF-κB DNA binding-inducing activity by EMSA and only band 2 (B2) corresponding to the 55 kDa protein (FIG. 2C lower panel) was able to elicit NF-κB DNA binding activity while buffer from the beginning or end of the salt gradient failed to activate NF-κB DNA binding activity.

Figure 3:
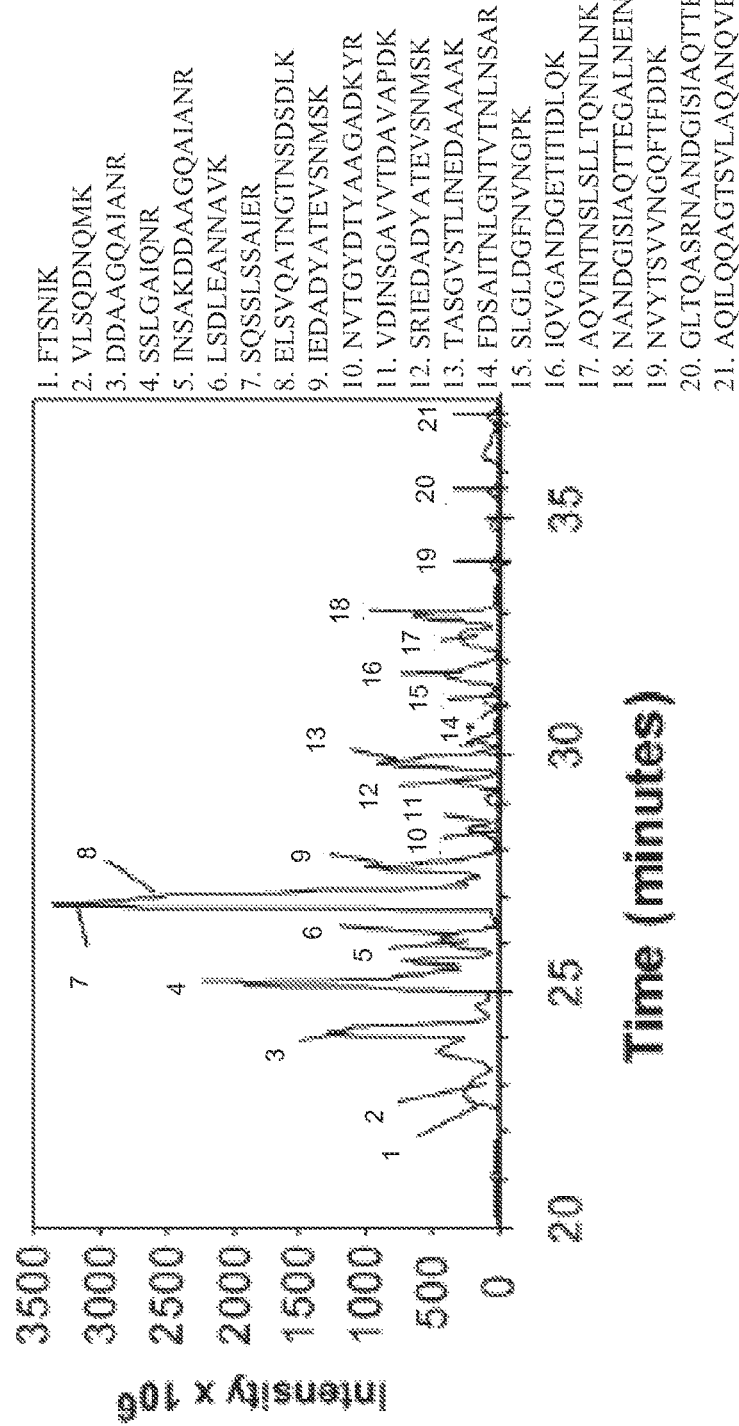
FIG. 3 demonstrates that the NF-κB activating factor in *Salmonella* culture broth is flagellin, as identified by mass spectrometry. Microcapillary HPLC tandem mass spectrometry of Band 2 digested by trypsin. Peaks corresponding to *Salmonella* peptides are numbered and identified with the corresponding numbered peptide sequence to the right.

Proteins corresponding to protein bands B1-B6 and blank areas of the gel were further processed for peptide sequencing. Trypsin digestion of the protein corresponding to B2 and analysis by electrospray ion trap LC/MS identified the amino acid sequence of twenty-one peptides. Flagellin (seventy-five percent coverage by the twenty-one peptides) was unambiguously identified as the protein consistent with inducing NF-κB DNA binding activity (FIG. 3).

Example 4

Flagellin is Required to Activate NF-κB in Intestinal Epithelial Cells

To determine if flagellin was indeed the factor that was responsible for triggering activation of NF-κB after exposure of intestinal epithelial cells to direct bacterial infection or to filtered culture broths of pathogenic *Salmonella*, we prepared infectious bacteria and boiled and filtered culture broths from the non-flagellated *E. Coli* DH5α, pathogenic *S. dublin* strain 2229, an isogenic *S. dublin* 2229 SopE$^-$ mutant, isogenic *S. dublin* 2229 SopB$^-$ mutant, isogenic *S. dublin* 2229 double SopE$^-$/SopB$^-$ mutant (strain SE1SB2), *S. typhimurium* strain 1103, and isogenic *S. typhimurium* fliC::Tn10 insertion mutant (strain 86) and a *S. typhimurium* 1103 isogenic double mutant fliC$^-$/fljB$^-$. SopE is a pathogenic *Salmonella* bacteriophage encoded protein that is injected into the host cell and acts as an exchange factor for the small Rho OTPases Rac1 and CdC42 initiating cytoskeleton rearrangements and eventual activation of the MAPK, SAPK and NF-κB pathways (7, 15), while SopB is a *Salmonella* protein that functions as an inositol phosphate phosphatase and participates in cytoskeletal rearrangements and stimulates host cell chloride secretion (44). Bacteria and culture broths were used to challenge HT29 intestinal epithelial cells and WCE extracts were prepared after forty-five minutes and analyzed for NF-κB DNA binding activity by EMSA. *Salmonella* strains could activate NF-κB while *Salmonella* strains failing to produce flagellin (fliC and fliC$^-$/fljB$^-$ mutants as indicated) also failed to activate NF-κB (FIGS. 4A & B). *E. Coli* DH5α is non-flagellated and does not produce flagellin failed to activate NF-κB. We also noticed through numerous experiments that *S. dublin* direct infections always activated NF-κB to a greater extent than *S. typhimurium* as observed in FIG. 4A while culture broths from both species activated NF-κB almost equally well (FIG. 4B). We believe this difference is due perhaps to *S. dublin* releasing more flagellin into the cell culture media than *S. typhimurium* during infection since purification of flagellin from both *S. dublin* and *S. typhimurium* and addition of equivalent amounts of chromatographically purified flagellin gave similar NF-κB activation profiles. Of note is the total failure of the double flagellin gene mutants to activate NF-κB as compared to the very minor activation observed in the single Phase I flagellin fliC::Tn10 insertion mutant (next to last lanes in FIGS. 4A & B) which likely is due to the extremely limited expression of the phase II flagellin (from fljB), although the strains of *Salmonella* used here genetically are unable or rarely shift phases of flagellin production. Since flagellin appears required for activation of the NF-κB pathway upon direct infection of intestinal epithelial cells it appeared possible that flagellin may also be the major determinant of other major mitogenic and stress activated signaling pathways activated upon pathogenic *Salmonella* infection of intestinal epithelial cells. Direct *Salmonella* infection of intestinal epithelial cells results in JNK activation (8) and also the activation of NF-κB via IKK (3).

Example 5

Figure 4:
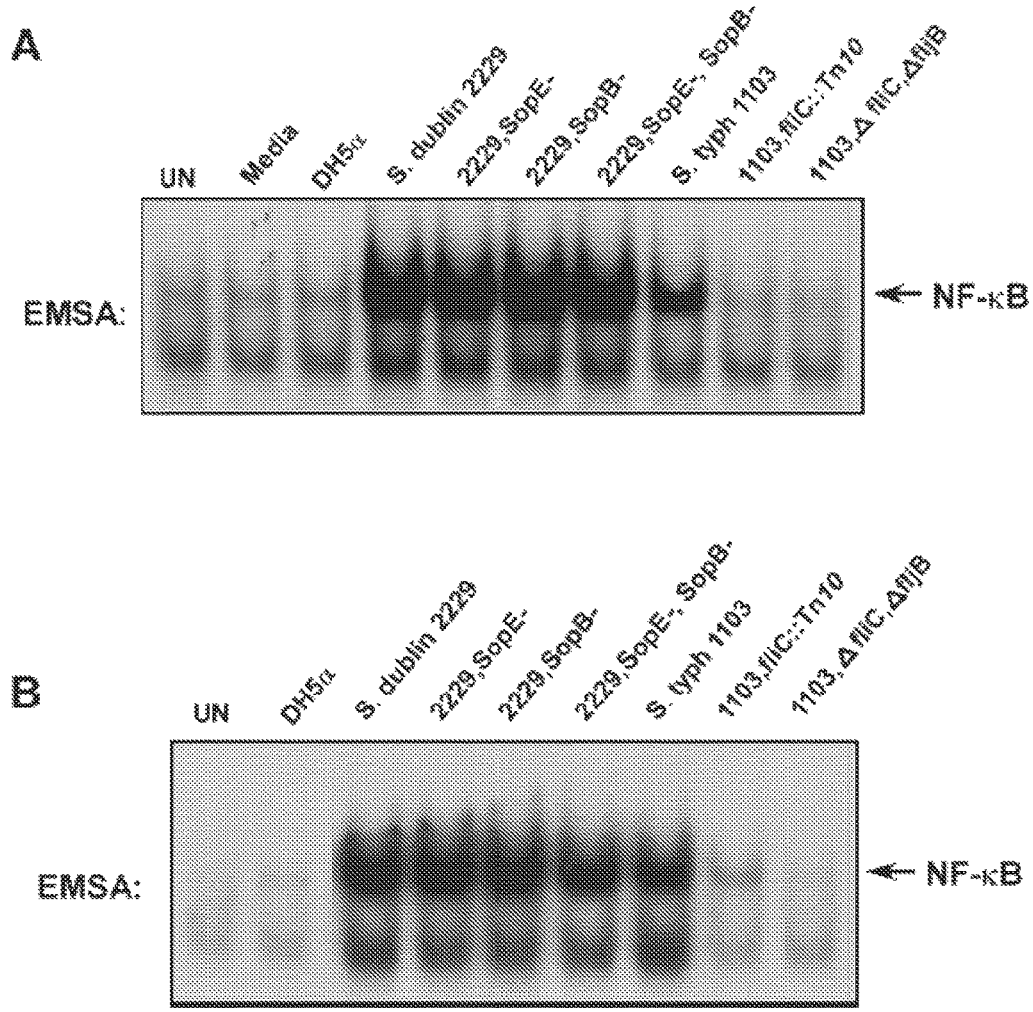
FIG. 4 demonstrates that flagellin mutants fail to activate NF-κB. Panel A: EMSAs assaying for NF-κB DNA binding activity in WCEs prepared 45 min from non-infected cells (UN) and after direct infection of HT29 cells with wild-type *E. coli* DH5α, wild-type *Salmonella dublin* or SopE⁻ mutant, SopB⁻ mutant, the SopE⁻/SopB⁻ double mutant, wild-type *Salmonella typhimurium* strain 1103, the fliC⁻ mutant (fliC::Tn10), the fliC⁻/fljB⁻ double mutant as indicated at an MOI of 50. Panel B: EMSAs assaying for NF-κB DNA binding activity in WCEs prepared 45 min after challenge of HT29 cells from non-infected cells (UN) or with sterile-filtered concentrated culture broths from wild-type and mutant bacteria as indicated.
Figure 5:
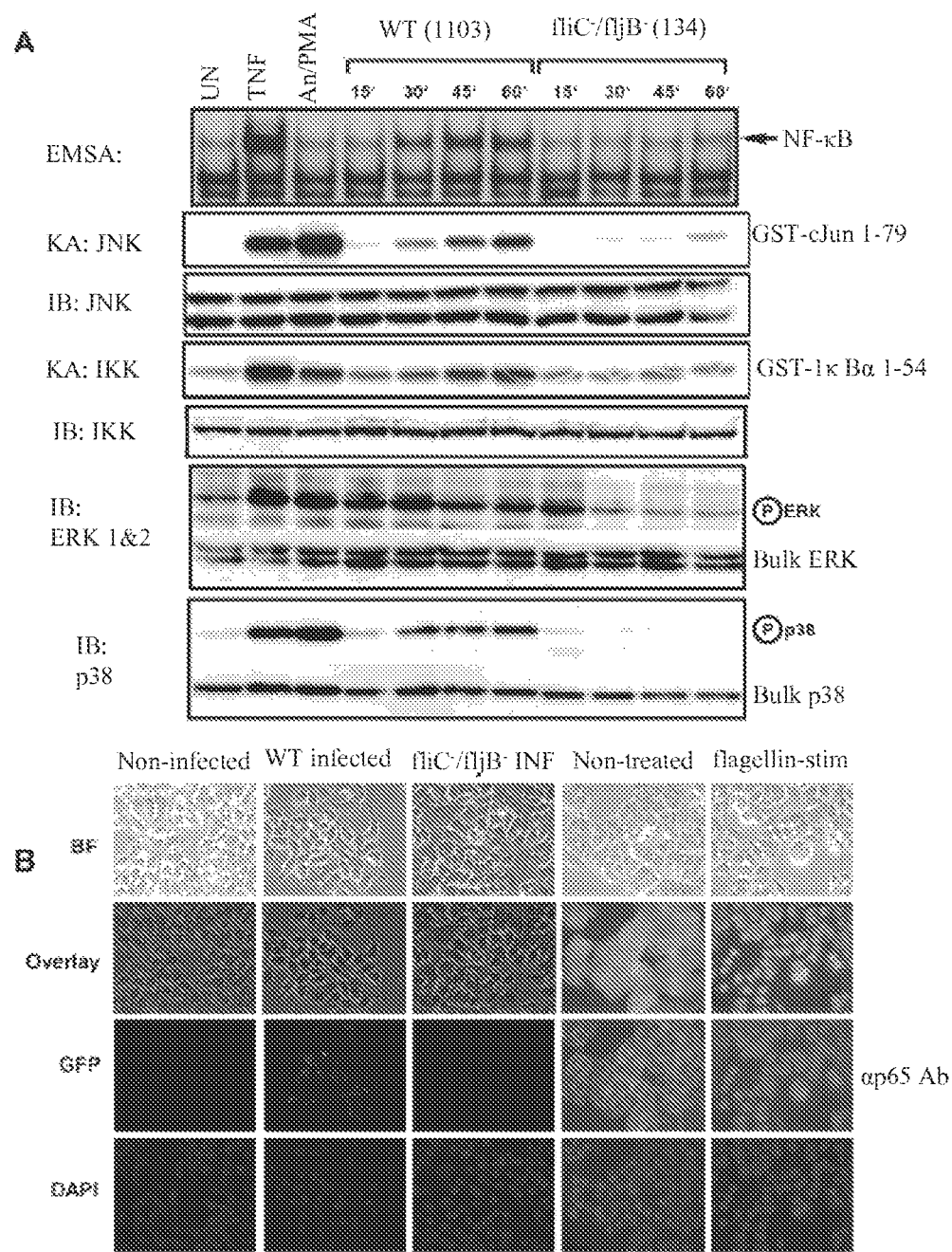
FIG. 5 demonstrates that flagellin is required for activating multiple signaling pathways during *Salmonella* infection and leads to nuclear localization of NF-κB. Panel A: HT29 cells were left untreated, stimulated with TNFα (10 ng/ml) or a cocktail of anisomycin [An] (20 µg/ml)/PMA (12.5 ng/ml) for 15 min, or infected with either wild-type (WT) *Salmonella typhimurium* strain 1103 or the *Salmonella typhimurium* double fliC⁻/fljB⁻ mutant strain 134 as indicated. WCE were prepared at the indicated times or at 10 min for TNF-treated cells or 15 min for anisomycin/PMA treated cells and used in EMSAs to analyze NF-κB DNA binding activity, or in immuno-kinase assays (KA) using anti-IKK or anti-JNK antibodies to measure IKK and JNK kinase activity on their respective substrates GST-IκBα 1-54 and GST-cJun 1-79 (as indicated). Immunoblot (IB) analysis of equivalent amounts (40 g) of protein from each extract was fractionated on SDS-PAGE gels and transferred to PVDF membranes and probed with the indicated antibodies to detect bulk IKK, JNK, ERK and p38 as indicated. Immunoblot analysis using phospho-specific antibodies for ERK and p38 to detect activated ERK and p38 are indicated. Panel B: Immunofluorescence demonstrating that flagellin mutant *Salmonella* fail to infect HT29 cells and that purified flagellin stimulation of HT29 cells leads to NF-κB nuclear p65 (RelA) localization as determined by indirect immunofluorescence. Imaging of the treatment indicated HT29 cells grown on coverslips was essentially the same as in FIGS. 1A & B. False coloring of the DAPI stain was used to enhance the visualization of both DAPI stained nuclei and p65 nuclear localization.

Flagellin Triggers Activation of the Mitogen Activated Protein Kinase, Stress Activated Protein Kinase and IKK Signaling Pathways Intestinal epithelial cells act as sentinels for invasion of luminal surfaces and orchestrate the attraction of effector immune cells to the area by production of chemokine genes like IL-8 and macrophage chemoattractant protein 1 (MCP1) proinflammatory cytokine genes such as TNFα, IL-1 and IL-6 (1, 4-6). Expression of these genes primarily depends upon the action of transcription factors that are activated in response to the transmission of signals via the MAPK, SAPK and IKK signaling pathways. Since NF-κB is considered a central regulator/activator of the proinflammatory gene program we decided to examine the effect that non-flagellin producing mutant strains of *Salmonella* had on activation of the MAPK, SAPK and IKK signaling pathways compared to infection of intestinal epithelial cells with wild-type *Salmonella* or by exposure of the intestinal epithelial cells to purified flagellin. Infection of HT29 cells with wild-type *S. typhimurium* resulted in activation of MAPKs ERK1&2, the SAPKs p38 and JNK and IKK (FIG. 5) as determined by use of activation-indicating phospho-specific antibodies in immunoblot (IB) analysis or antibody-specific immuno-kinase assays (KA) for JNK and IKK using their respective substrates GST-cJun 1-79 and GST-IκBα1-54. Interestingly, MAPK stimulation is transient in nature as activation declines beginning at forty-five minutes while p38, JNK and IKK activity increases with time through one hour. As seen in FIG. 4, the fliC/fljB-double mutant *Salmonella* also failed to induce IKK and NF-κB activity (FIG. 5 as indicated). Surprisingly, the fliC⁻/fljB⁻ double mutant *Salmonella* failed to induce the SAPKs p38 and JNK and only briefly (fifteen minutes) activated MAPK. This result is puzzling since other *Salmonella* proteins such as SopE and SopE2 can activate the small GTPases Rac and CdC42, and these Rho family GTPases have been linked to JNK and p38 activation (7, 8, 14, 15) yet appear not to function in the flagellin minus strain.

The fliC⁻/fljB⁻ double mutant *Salmonella* failed to invade HT29 cells compared to the wild-type *Salmonella* strain as determined by gentamycin protection/invasion assay. The flagellin fliC⁻/fljB⁻ double mutant displayed a four orders of magnitude difference in its ability to invade HT29 cells. To demonstrate this point further, we infected HT29 cells with either wild-type *Salmonella* or the fliC⁻/fljB⁻ double mutant *Salmonella* (strain 134), both strains were transformed with the plasmid pFM10.1 that encodes GFP under the control of the *Salmonella* ssaH promoter and only functions once the bacteria has invaded the host cell (10, 36). The wild-type *Salmonella* clearly was able to infect HT29 cells (GFP, FIG. 5B) while the flagellin mutant bacteria failed to invade HT29 cells as evidenced by the lack of GFP expression (FIG. 5B). To determine if flagellin is sufficient or that other bacterially produced proteins are required for invasion, we added either purified flagellin or sterile-filtered culture broths or a combination of both to HT29 cells that were challenged with the *Salmonella* fliC/fljB double mutant and assayed for invasion. Intestinal epithelial cells failed to be invaded using all tested combinations of purified flagellin and/or culture broths with the fliC⁻/fljB⁻ double mutant strain². There is not believed to be a direct connection between flagellin genes and the effectiveness of the type III secretion system to deliver bacterially produced proteins such as SopE, SopE2 and SipA or other Sip proteins (7, 14, 15, 45, 46) that play important roles in initiating bacterial internalization. Furthermore, to evaluate the effectiveness of flagellin to stimulate p65 (RelA) nuclear localization in intestinal epithelial cells we challenged HT29 cells with purified flagellin and examined p65 (RelA) localization using indirect immunofluorescence and found p65 (RelA) nuclear localization in nearly every cell (FIG. 5B as indicated).

Purified flagellin (0.5 g/ml) potently activated NF-κB in HT29 cells similar to that observed for TNF (10 ng/ml) treatment of HT29 cells in a time dependent manner (FIG. 6A) when WCE were prepared at the various times as indicated after exposure and assayed for NF-κB DNA binding activity in EMSAs. Analysis of the MAPK, SAPK and IKK signaling pathways (FIG. 6B) in these same extracts using activation-specific phospho-antibodies to monitor MAPK and p38 kinase activation or antibody-specific immunoprecipitation kinase assays for JNK and IKK activities demonstrated that JNK and IKK activity increased through time to one-hour while p38 and MAPK (ERK1&2) activity peaked at thirty minutes and began to decline to noticeably lower levels by one-hour (FIG. 6B as indicated). The activation profile of the MAPK, SAPK and IKK signaling molecules ERK1&2, p38, JNK and IKK in intestinal epithelial cells in response to purified flagellin exposure remarkably resembled that of intestinal epithelial cells infected with wild-type *Salmonella* (FIG. 5A). From these observations we conclude that the temporal activation of the signaling pathways examined here (MAPK, SAPK and IKK), which reflect early events in *Salmonella* infection, are determined almost exclusively by recognition and response of intestinal epithelial cells to flagellin.

We wished to further examine the effect of purified flagellin and flagellin present on *Salmonella* on the temporal pattern of proinflammatory cytokine gene expression in intestinal epithelial cells in order to differentiate the effects of flagellin alone vs. flagellated *Salmonella* or non-flagellated *Salmonella* infection. HT29 cells were left untreated, stimulated with TNFα (10 ng/ml), or stimulated with flagellin (0.5 ug/ml), or infected with wild-type *Salmonella typhimurium* or the *Salmonella* fliC/fljB double mutant (at MOI of 50). After the indicated times after treatment or infection, HT29 cells were harvested in ice-cold PBS and the cell pellets lysed in Trizol and RNA was purified and used to prepare first-strand cDNA (see Experimental Procedures). Aliquots of the cDNA were used in semi-quantitative RT-PCR reactions using IL1α, IL-1β, IL-8, TNFα, MCP1 and β-actin gene specific primers (sequences available upon request) and the products were fractionated on ethidium bromide containing 1.2% agarose gels. Expression of the known NF-κB target genes IL-1β, IL-8, TNFα and MCP1 was increased in response to TNFα or purified flagellin exposure (FIG. 6C). Wild-type *Salmonella* infection also led to activation of these same genes although the expression of TNFα and MCP1 was transient in comparison and occurred immediately after infection. The *Salmonella* fliC⁻/fljB⁻ double mutant failed to induce IL-1β, IL-8 and TNFα expression, however MCP1 expression was induced, although at lower levels than that induced by wild-type *Salmonella*, and also, the expression of MCP1 was not transient in nature but continued throughout the time course (9 h) (FIG. 6C). The expression level of β-actin served as an internal standard for comparison. Interestingly, IL-1α, which is not an NF-κB target gene was stimulated in response to HT29 cell challenge by all of the treatments. Obviously, the *Salmonella* fliC⁻/fljB⁻ double mutant can activate other unknown signaling pathways leading to IL-1α expression.

Example 6

Flagellin Activates NF-κB DNA Binding in an MyD88-Dependent Manner

Figure 7:
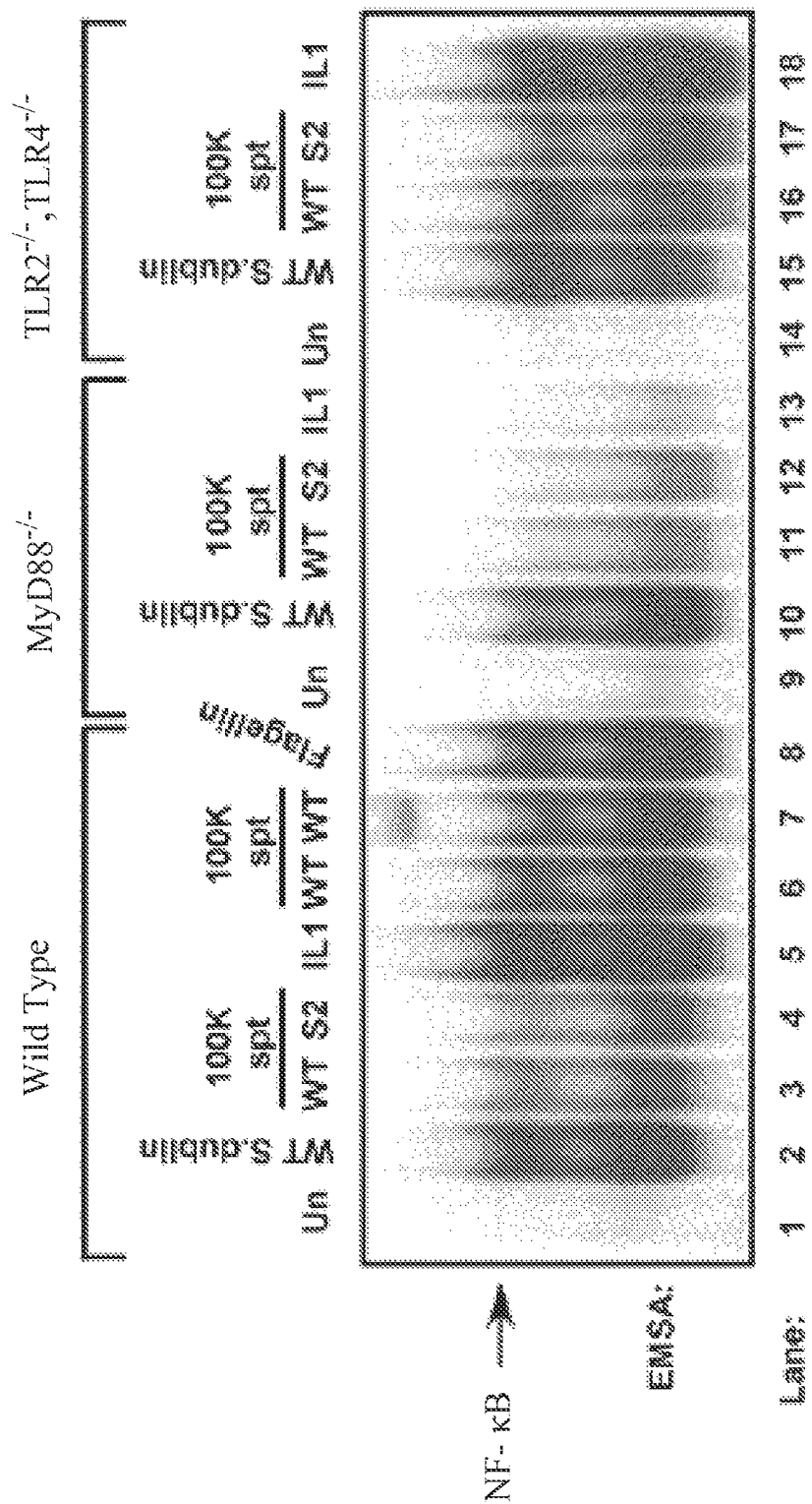
FIG. 7 demonstrates that flagellin-mediated activation of NF-κB is MyD88 dependent. Infectious wild-type *Salmonella dublin* (MOI of 100), IL-1 (20 ng/ml), purified flagellin (1 µg/ml) (as indicated), sterile-filtered and concentrated 100 kDa filter retentate supernatant (spt) from wild-type *Salmonella dublin* and SopE⁻/SopB⁻ double mutant *Salmonella dublin* strain SE1SB2 (S2, as indicated) was used to challenge wild-type, MyD88⁻/⁻ knockout or TLR2⁻/⁻/TLR⁻/⁻ double knockout MEFs as indicated. WCEs were prepared 45 min after treatments and examined by EMSA to analyze NF-κB DNA binding activity. IL-1 (20 ng/ml) was used as a positive control to monitor MyD88 function.

Since flagellin was capable of activating the requisite signaling pathways consistent with proinflammatory gene activation and this activity was reminiscent of the action of a cytokine like TNFα that activates all cells on which a functional cell surface receptor for it is present (see p65 [RelA] nuclear localization in FIG. 1 and FIG. 5C) we decided to examine the potential of the Toll-like receptors, known pathogen pattern recognition receptors, to activate the NF-κB pathway in response to flagellin exposure. To test this hypothesis we examined the effect that a dominant-negative MyD88 (aa 152-296) (47) expressing adenovirus had on flagellin-mediated NF-κB activation in HT29 cells. MyD88 is an adapter protein utilized by the IL-1 receptor and all of the known TLRs, which share homology to IL-1 through their cytoplasmic signaling domain and is required for immediate activation of the NF-κB pathway (48, 49). Expression of DN-MyD88 in HT29 cells blocked the activation of NF-κB DNA binding activity assayed by EMSA analysis in response to IL-1 or flagellin exposure, consistent with the action of a TLR-mediated activation of NF-κB. To examine this possibility further we initially used wild-type, MyD88⁻/⁻ and TLR2⁻/⁻/TLR4⁻/⁻ MEFs (a gift of S. Akira, Univ. of Osaka, JA) to verify the role of MyD88 and to examine the potential role of two of the TLRs to respond to flagellin or to direct wild-type *Salmonella* infection and lead to NF-κB activation (FIG. 7). Wild-type *Salmonella* infection activates NF-κB potently in both the wild-type and TLR deficient MEFs (lanes 2 & 15) but this activation is somewhat defective in the MyD88 deficient MEFs (lane 10). Challenge of all three types of cells with concentrated sterile-filtered wild-type *S. dublin* or the double SopE⁻/SopB⁻ isogenic mutant *S. dublin* strain SE1SB2 culture broths activated NF-κB in wild-type MEFs and TLR2/4 double deficient cells but failed to activate NF-κB in MyD88 deficient cells (compare lanes 11 and 12 with lanes 3, 4, 6, 7, 16 and 17). NF-κB was potently activated in wild-type MEFs by exposure to purified flagellin (0.5 g/ml) and therefore eliminated the possibility that LPS played a role in NF-κB activation in these experiments. The exclusion of LPS as a major contributor to NF-κB activation is also provided by the potent activation of the TLR2/4 double deficient MEFs (lanes 16 & 17). TLRs 2 and 4 respond to bacterial lipopeptides, peptidoglycans, certain LPSs and gram negative LPS respectively (50-52). IL-1 stimulation verified the functional requirement of MyD88 in transmission of IL-1 and flagellin-mediated signals.

To further define a possible role for the TLRs in flagellin recognition we assayed for the ability of overexpressed TLRs to activate NF-κB in cells that normally respond poorly to flagellin exposure. Choosing cells that responded slightly to purified flagellin ensured that the signaling components and adapters that flagellin uses were present and functional and that the limiting factor was likely only to be the receptor that responds to flagellin. We found that HeLa cells and HEK293T cells activated NF-κB DNA binding activity in response to IL-1 stimulation but poorly to flagellin exposure and we chose HEK293T cells to use further because of their greater transfection efficiency. Amino-terminus FLAG epitope-tagged TLRs 1-9 (kind gifts of R. Medzhitov, Yale Univ. and R. Ulevitch, TSRI) (42, 43) were overexpressed in HEK 293T cells in transient transfections along with the 2×-NF-κB-dependent promoter driven luciferase reporter gene and the expression of luciferase in response to no treatment, flagellin (0.5 μg/ml) or TNFα (10 ng/ml) was determined. TLR5 was the only TLR whose expression resulted in a noticeable response to flagellin challenge of the cells (Table 1).

To further determine the likelihood of TLR5 being the TLR through which flagellin activated NF-κB, we constructed dominant-negative signaling mutations by deletion of the carboxyl portion of each TLR to a conserved tryptophan in the TIR domain. A similar mutation in the IL-1 receptor abrogates its ability to lead to NF-κB activation (54, 55). Each DN-TLR along with a reverse cloned TLR5 (AS-TLR5) was cloned into the mammalian expression vector pCDNA3.1 (Invitrogen). All mutant proteins were expressed well. Each DN-TLR mammalian expression vector and empty expression vector along with 2×NF-κB Luc was transfected as previously described (3) into HT29 cells which respond very well to flagellin. The transfected cells were left untreated, stimulated with TNFα (10 ng/ml) or with purified flagellin (0.5 μg/ml). Reporter gene expression was observed not to be affected by DN-TLR expression in response to TNFα stimulation of transfected cells (FIG. 8A); however, only expression of either the DN-TLR5 or an antisense TLR5 construct resulted in a nearly fifty percent and twenty-five percent inhibition of flagellin-mediated reporter gene activation respectively (FIG. 8B), while DN-TLR2 also was found to mildly inhibit flagellin-mediated reporter expression. These results imply that TLR5 takes part in cell surface recognition of flagellin and initiates the signaling pathway leading to NF-κB activation. The effect of DN-TLR2 on NF-κB-dependent reporter gene activation may be non-specific since its expression also inhibited TNFα-mediated reporter activation as compared to the other DN-TLRs. DN-TLR2 may also compete for an unknown adapter protein that both TLR2 and TLR5 might share. In any event, TLR2 and TLR4 were shown by the results presented in FIG. 7 not to be required for flagellin-mediated activation of NF-κB.

Example 7

Figure 9:
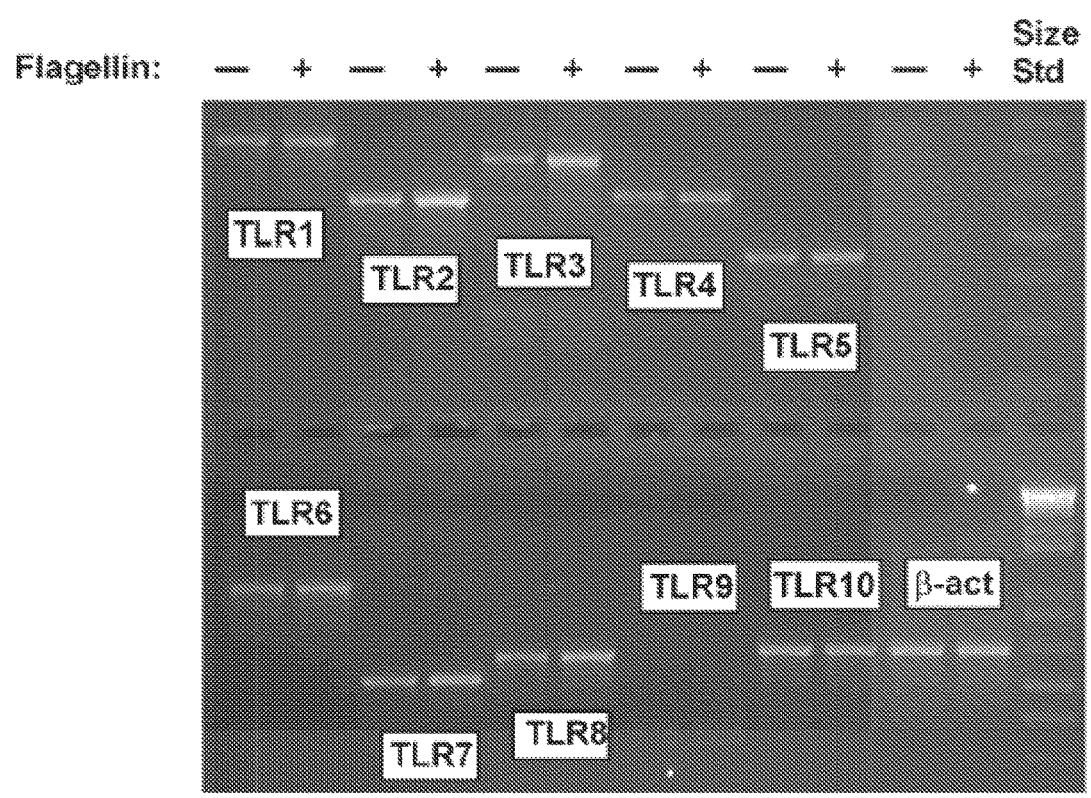
FIG. 9 demonstrates that flagellin stimulation of intestinal epithelial cells leads to activation of a subset of TLR genes. HT29 cells were stimulated with flagellin (1 mg/ml) and RNA was isolated after 3 h using Trizol and used to make first strand cDNA. RT-PCR products generated using gene-specific primers for each TLR as indicated are pictured. β-actin was used as a standard for normalizing expression patterns.

Flagellin-Mediated Activation of NF-κB Leads to Increased Expression of a Subset of TLRs Stimulation of intestinal epithelial cells with *S. typhimurium* or with purified flagellin led to activation of the proinflammatory gene program (FIG. 6C). We wished to examine whether or not expression of TLR genes would also be altered in flagellin-stimulated cells. HT29 cells were treated with purified flagellin (0.5 μg/ml) and total RNA was isolated from non-treated and treated cells three hours after stimulation and used to make first-strand cDNA. Semi-quantitative RT-PCR using gene-specific primers for each of the TLRs and first-strand cDNA prepared from non-stimulated or flagellin stimulated cells was used to generate DNA products that were fractionated on ethidium bromide containing 1.2% agarose gels. TLRs 2, 3 and 7 were increased in expression after flagellin stimulation (FIG. 9). The expression pattern of the other TLRs remained unchanged, β-actin expression served as an internal abundance control.

TLR5 is expressed in cells that don't respond well to flagellin. This study and others (22, 33) have identified TLR5 as the likely TLR through which flagellin activates NF-κB. Previous reports made no determination on the presence or abundance of TLR5 in the cells that they used to ascertain its function (22, 33). We wished to determine if TLR5 protein abundance was absent or greatly decreased in cells that failed to respond or responded poorly to challenge by flagellin. TLR5 abundance in a number of cell lines was examined by immunoblot analysis using a TLR5-specific antibody and compared with the ability of purified flagellin to induce NF-κB DNA binding activity of WCEs prepared from them. Intestinal epithelial cell lines T84 and HT29 were used as was the lung adenocarcinoma cell line A549, the human cervical adenocarcinoma cell line HeLa, the human embryonic kidney cell line expressing large T antigen HEK293T, and the glioblastoma cell line T98G. TLR5 protein was detected in all cell lines examined by immunoblot with TLR5-specific antibody (FIG. 10A). T84 cells exhibited the highest abundance while expression levels of the other cell lines were similar and appeared not to differ by more than two-fold (FIG. 10A). NF-κB DNA binding activity in non-stimulated, TNFα and flagellin stimulated cells was analyzed by EMSA assays of WCEs prepared from each cell type (FIG. 10B). HT29 and A549 cells responded strongly to flagellin and to TNFα stimulation while HeLa, 293T and T98G cells responded poorly (HeLa, 293T) or not at all (T98G) to flagellin stimulation. The authenticity of the NF-κB DNA binding complex was determined using p65-specific antibody to supershift the NF-κB DNA:protein complex. It is of interest that some cells that express TLR5 either do not respond at all or do so very poorly. This may be due to either lack of receptor presence at the plasma membrane and intracellular localization, inactivating or detrimental mutations in the TLR5 gene in these cell lines or lack of or low abundance of a required co-receptor or adapter protein (as is the case in some cells for TLR4 and its co-receptor/adapter MD2 (30, 56, 57)). IL-1 can activate NF-κB DNA binding activity in all of the examined cell lines so it appears that the signaling apparatus downstream of MyD88 to NF-κB is intact.

Example 8

Isolation of Recombinant Flagellin

Figure 13:
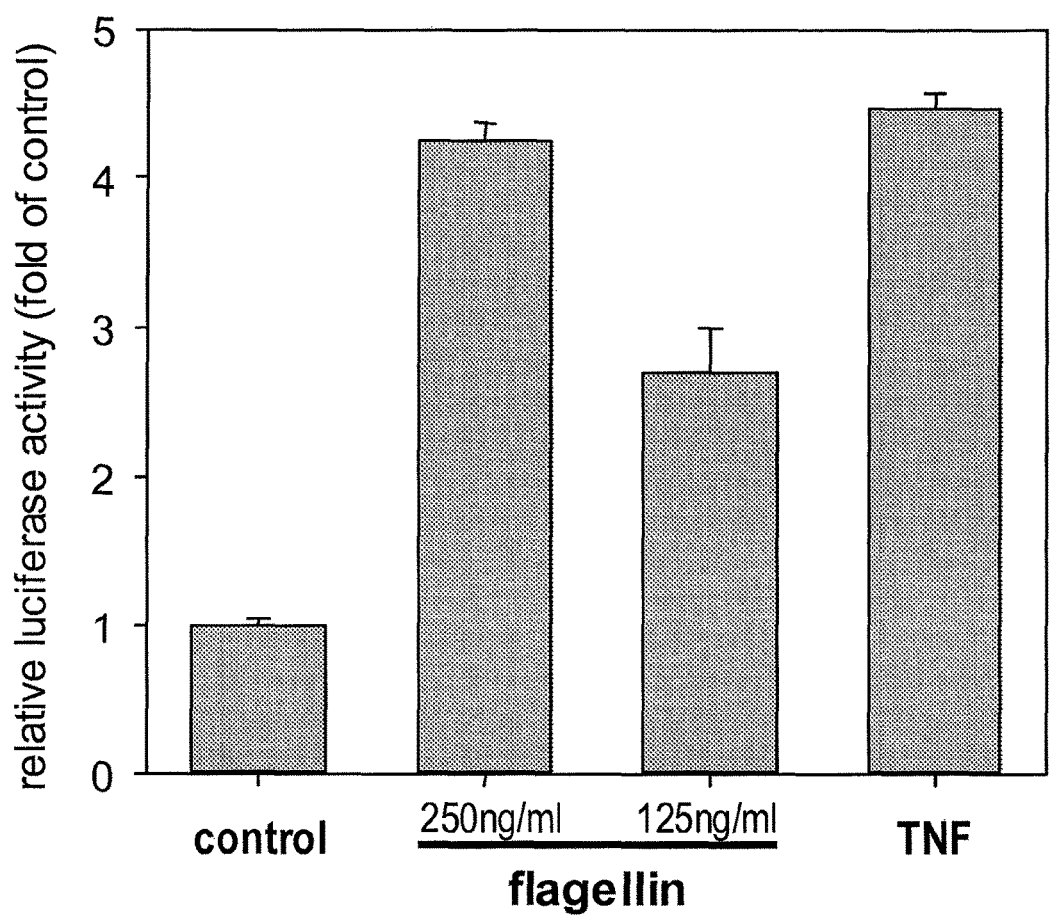
FIG. 13 demonstrates that recombinant flagellin is capable of NF-κB activation.

In order to confirm that recombinant flagellin was able to induce NF-κB, it was tested for activity using reporter cells carrying NF-κB-responsive luciferase (luc). The reporter construct contains three NF-κB-binding sites from the E-selectin promoter combined with the Hsp70 minimal promoter and is routinely used for the detection of NF-κB. Luciferase activity was measured in cell lysates 6 hours after addition of flagellin into the medium. TNFα was used as a positive control. The results of a representative experiment are shown in FIG. 13 and indicate that recombinant flagelling is capable of NF-κB activation.

Example 9

Flagellin Delays Mouse Death Caused by IR-Induced GI Syndrome

As indicated above, flagellin is a potent activator of NF-κB and presumably can act as an inhibitor of apoptotic death. Since cytokines capable of inducing NF-κB act as radioprotectants, we tested whether flagellin might also serve as a radioprotectant.

Figure 14:
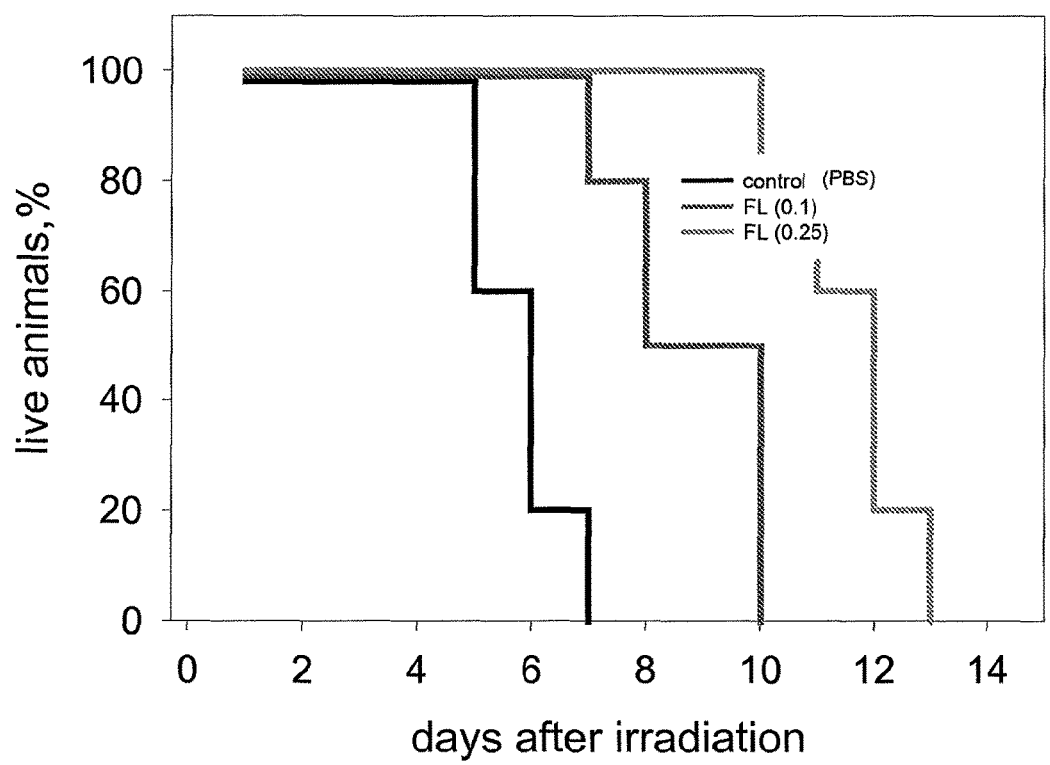
FIG. 14 shows a representative experiment testing the ability of flagellin to protect mice from radiation. C56BL6 mice (6 week old males, 10 animals per group) were injected i.v. with 2.0 μg (0.1 mg/kg) or 5 μg (0.25 mg/kg) of flagellin in PBS. Four hours later, mice were irradiated with 15 Gy and mouse survival was monitored daily.

Whole body irradiation of mice with 15 Gy gamma radiation leads to death within 8 days from GI syndrome providing a conventional model of radiation induced damage of GI tract (see above). To test whether flagellin is capable of protecting GI epithelium from IR, we tested the effect of i.v.-injected flagellin on the dynamics of mouse lethality after 15 Gy of radiation. We used a range of flagellin doses, all of which were significantly lower than the highest tolerable dose known from literature (300 μg/mouse, Eaves-Pyles T, et al 2001b). Irradiation was done 4 hours post treatment. The results of a representative experiment are shown in FIG. 14. As expected, control irradiated mice (that received PBS iv.) died between 5 and 8 days post-treatment, while animals that received flagellin lived significantly longer, the extension of animal survival correlated with the dose of flagellin. Pathomorphological analysis of the small intestine on day 7 after irradiation reveals dramatic difference between flagellin-treated and control groups (FIG. 15). Intravenous, intraperitoneal and subcutaneous delivery of 0.2 mg/kg of flagellin followed by 13 Gy irradiation afforded similar degree of protection, leading to 85-90% 30-day survival of mice (data not shown). Experiments were performed essentially as described above for optimal dosage experiments but with 13 Gy irradiation and varied routes of delivery.

Example 10

Flagellin Rescues Mice from Lethal IR-Induced Hematopoietic Syndrome

Figure 16:
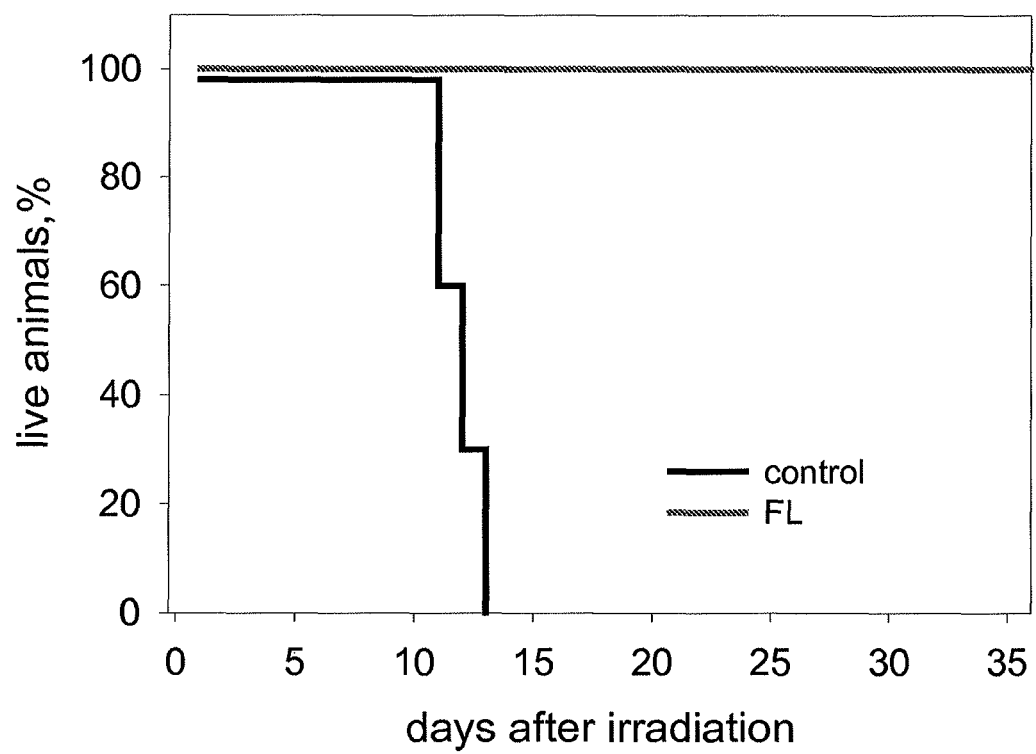
FIG. 16 shows the effect of flagellin on mouse sensitivity to 10Gy of total body gamma radiation.

We next tested whether flagellin has an effect on mouse IR-induced death from HP syndrome that is experimentally induced by lower radiation doses (usually up to 11 Gy) that are incapable of causing lethal GI toxicity. The experiments were done similarly to the above-described ones (FIGS. 14 and 15), however, instead of 15Gy, mice received 10Gy, the dose that caused 100% killing in control group by day 13 (FIG. 16). Flagellin-treated group (5 μg/mouse) showed complete protection from this dose of IR indicating that flagellin-mediated radioprotection acts not only against GI but also against HP IR-induced syndromes.

Example 11

Time Dependence on the Protective Effect of Flagellin

Figure 17:
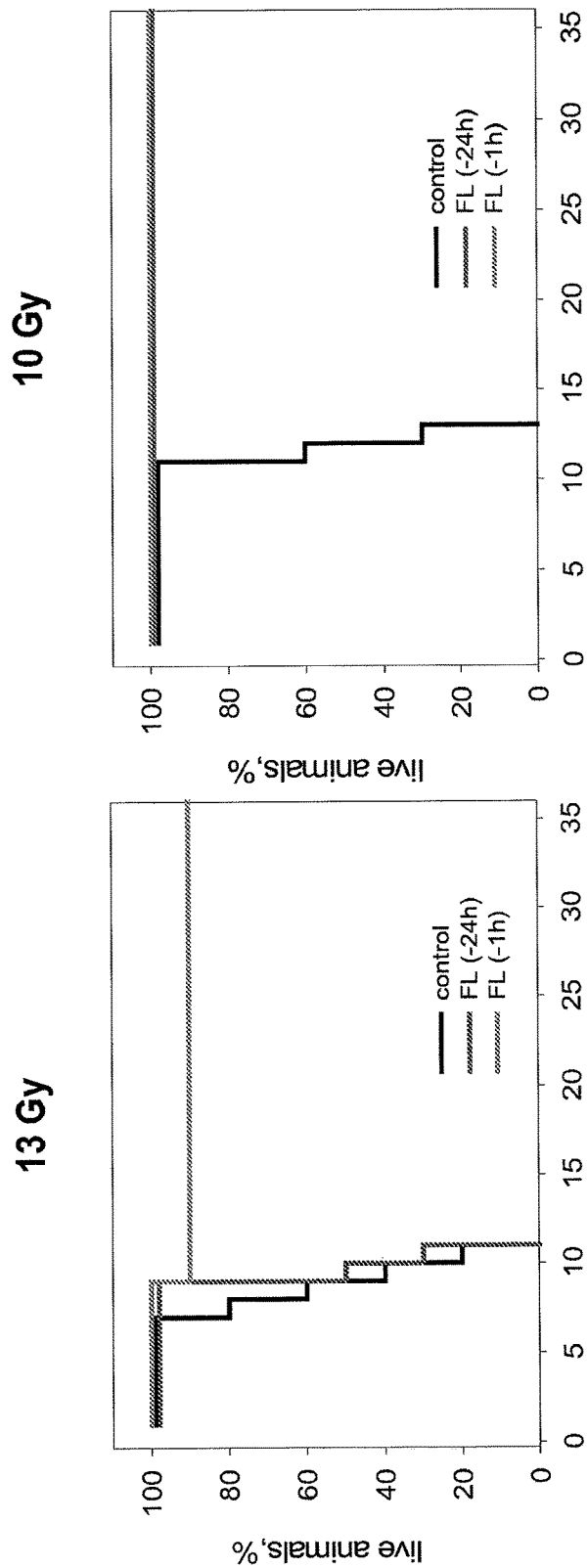
FIG. 17 shows the effect of flagellin injected i.v. at indicated times before irradiation on mouse sensitivity to 13Gy (left) and 10Gy (right) of total body gamma radiation.

In order to estimate the dependence of radioprotective activity of flagellin on the time of treatment by injecting mice at different times before 13Gy of gamma irradiation. The results of one of such experiments is shown in FIG. 17, The obtained results show that flagellin is effective as radioprotectant from 13Gy if injected 1-4 h before treatment but is no longer effective if injected 24 h before irradiation.

In order to estimate the dependence of radioprotective activity of flagellin on the time of treatment, mice were injected at several time points relative to the moment of gamma-irradiation.

Experiments were done essentially as explained above, using intraperitoneal injection of 5 μg/mouse (0.2 mg/kg) of CBLB-501 or, for control mice, 5 μg/mouse (0.2 mg/kg) of bacterial RNA polymerase. The experiments were performed on NIH-Swiss mouse strain. The results show that flagellin –501 provides ~90% survival after 13 Gy irradiation if injected at 1 or 2 hours before treatment (FIG. 17). Only –1 h graph is shown for clarity, however, both time-points (–1 and –2 h) provide similar degree and dynamics of survival. 4 h timepoint shows somewhat lower protection. Flagellin injected 24 hours before irradiation had no protective effect against 13 Gy induced death.

Interestingly, administration of flagellin 24 hours before 10 Gy gamma-irradiation provided 100% protection. While 13 Gy irradiation in mice primarily induces death from GI syndrome, 10 Gy-induced death is mostly mediated by hematopoietic syndrome. Accordingly, such long-term protection from 10 Gy irradiation may be mediated by enhanced proliferation or survival of hematopoietic stem cell induced by flagellin and/or long-living secondary cytokines.

Example 12

Determination of $LD_{50/30}$, $LD_{50/7}$ and DMF for Flagellin

We obtained an estimate of radiation dose-dependent protection for flagellin. As shown above (FIG. 17), treatment with flagellin was sufficient for 100% protection against 10 Gy gamma-irradiation (this dose causes death from hematopoietic syndrome) and 90% 30-day survival at 13 Gy (both hematopoietic and GI syndromes). Experiments were performed as described above, using flagellin 5 μg/mouse (0.2 mg/kg), intraperitoneally injected 1 h before irradiation.

Figure 18:
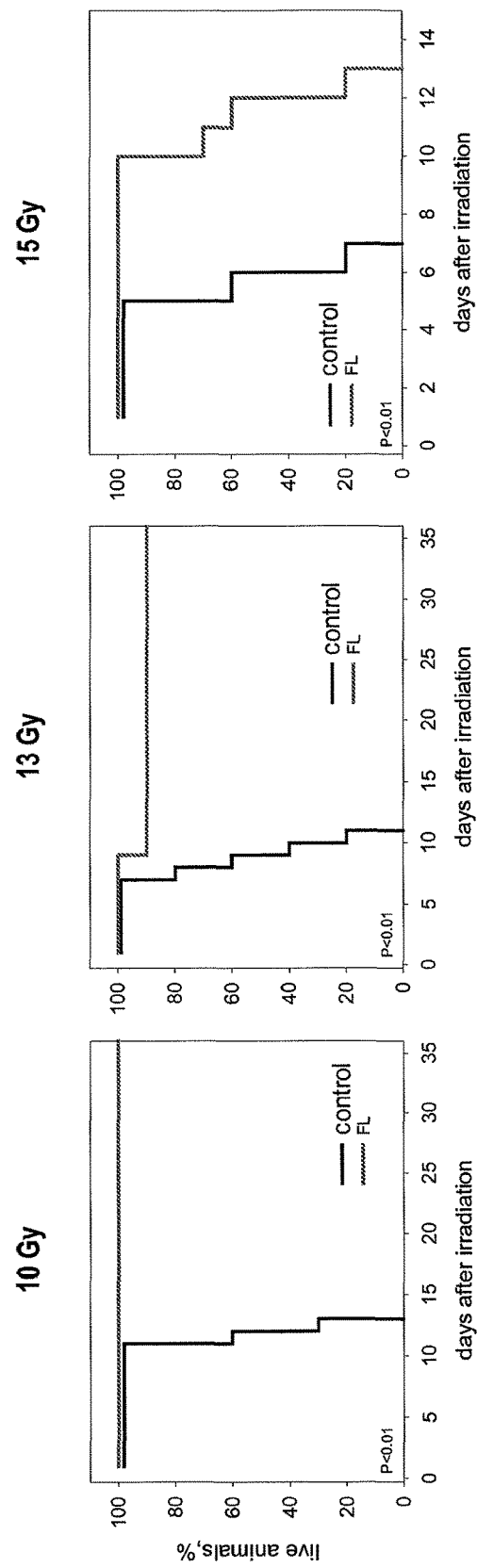
FIG. 18 shows the effect of flagellin on mouse sensitivity to 10, 13 and 15 Gy of total body gamma radiation.

At 15 Gy, however, 100% 7-day survival was followed by delayed death after 13 days (0% 30-day survival), while control group had fully succumbed to GI syndrome by day 7 (FIG. 18). The kinetics of CBLB-501 treated group mortality after 15 Gy irradiation is reminiscent of such of control group at 10 Gy, hinting at death caused by hematopoietic syndrome. The results provide an estimate of flagellin $LD_{50/30}$ around 13.5-14 Gy and $DMF_{30}$ of about 1.75-1.8. This degree of radioprotection is significantly higher than any reported for a natural compound.

The invention claimed is:

1. A method of treating a mammal suffering from stress-mediated damage to normal tissue, the method comprising administering to a subject in need thereof a therapeutically effective amount of composition comprising flagellin, wherein the stress is attributable to whole body radiation.

2. The method of claim 1 wherein the composition is administered prior to, together with, or after the tissue damage.

3. The method of claim 1, wherein the flagellin is capable of inducing NF-κB activity.

4. The method of claim 3, wherein the induction of NF-κB is TLR-mediated.

* * * * *